United States Patent
Buchberger

(10) Patent No.: US 11,253,671 B2
(45) Date of Patent: Feb. 22, 2022

(54) INHALER COMPONENT

(71) Applicant: BATMARK LIMITED, London (GB)

(72) Inventor: Helmut Buchberger, Ennsdorf (AT)

(73) Assignee: NICOVENTURES TRADING LIMITED, London (GB)

( * ) Notice: Subject to any disclaimer, the term of this patent is extended or adjusted under 35 U.S.C. 154(b) by 1250 days.

(21) Appl. No.: 15/454,156

(22) Filed: Mar. 9, 2017

(65) Prior Publication Data

US 2017/0173278 A1 Jun. 22, 2017

Related U.S. Application Data

(63) Continuation of application No. 14/235,210, filed as application No. PCT/EP2012/003103 on Jul. 24, 2012, now Pat. No. 9,623,205.

(30) Foreign Application Priority Data

Jul. 27, 2011 (AT) ................. A 1095/2011

(51) Int. Cl.
*A61M 16/10* (2006.01)
*A24F 47/00* (2020.01)
(Continued)

(52) U.S. Cl.
CPC .......... *A61M 16/109* (2014.02); *A24F 40/42* (2020.01); *A24F 40/44* (2020.01); *A24F 40/46* (2020.01);
(Continued)

(58) Field of Classification Search
None
See application file for complete search history.

(56) References Cited

U.S. PATENT DOCUMENTS 228,598 A 6/1880 Buckley
353,327 A 11/1886 Randolph
(Continued)

FOREIGN PATENT DOCUMENTS

AT 507187 A4 3/2010
AT 507187 B1 3/2010
(Continued)

OTHER PUBLICATIONS

Aerosols, "Pulmonary Pharmacology: Delivery Devices and Medications," Sep. 6, 2017, available at www.cdeu.org/cecourses/z98207/ch4.html, 2 pages.
(Continued)

*Primary Examiner* — Kathryn E Ditmer
(74) *Attorney, Agent, or Firm* — Patterson Thuente Pedersen, P.A.

(57) ABSTRACT

The invention relates to an inhaler component for forming a vapor/air mixture or/and condensation aerosol by evaporation of a liquid material and, if appropriate, condensation of the formed vapor, comprising: an electric heating element for evaporating a portion of the liquid material; a wick with a capillary structure, which wick forms a composite with the heating element and automatically supplies the heating element with the liquid material; a carrier plate, preferably a printed circuit board, which carries the composite and on which the heating element is electrically contacted; a capillary gap formed at least partially by the carrier plate and automatically supplying the composite with the liquid material, by means of an end portion of the wick extending into the capillary gap; a liquid container which contains the liquid material and from which the capillary gap draws the liquid material. In order to achieve a compact overall arrangement, it is proposed that the capillary gap at least
(Continued)

partially covers the liquid container on the outside, in a view perpendicular to the carrier plate.

6 Claims, 15 Drawing Sheets

(51) Int. Cl.
    *A61M 15/06*         (2006.01)
    *A61M 11/04*         (2006.01)
    *A61M 16/14*         (2006.01)
    *A61M 15/00*         (2006.01)
    *A24F 40/42*         (2020.01)
    *A24F 40/44*         (2020.01)
    *A24F 40/46*         (2020.01)
    *A24F 40/485*        (2020.01)
    *A24F 40/10*         (2020.01)

(52) U.S. Cl.
    CPC ......... *A24F 40/485* (2020.01); *A61M 11/041* (2013.01); *A61M 11/042* (2014.02); *A61M 15/0021* (2014.02); *A61M 15/06* (2013.01); *A61M 16/145* (2014.02); *A24F 40/10* (2020.01); *A61M 2205/12* (2013.01); *A61M 2205/583* (2013.01); *A61M 2205/8206* (2013.01)

(56) References Cited

U.S. PATENT DOCUMENTS

| | | |
|---|---|---|
| 576,653 A | 2/1897 | Bowlby |
| 595,070 A | 12/1897 | Oldenbusch |
| 744,074 A | 11/1903 | Hiering |
| 799,844 A | 9/1905 | Fuller |
| 885,374 A | 4/1908 | Pohlig |
| 1,163,183 A | 12/1915 | Stoll |
| D53,386 S | 5/1919 | Thomas |
| 1,436,157 A | 11/1922 | Fazio, I |
| 1,807,936 A | 6/1931 | Saunders |
| 1,815,069 A | 7/1931 | Petro |
| 1,937,120 A | 11/1933 | Julius et al. |
| 1,937,987 A | 12/1933 | Sexton |
| 2,057,353 A | 10/1936 | Whittemore |
| 2,262,318 A | 11/1941 | Fox |
| 2,371,006 A | 3/1945 | Weaver |
| 2,411,946 A | 12/1946 | Max et al. |
| 2,467,923 A | 4/1949 | Allen |
| 2,483,304 A | 9/1949 | Rudolf et al. |
| 2,522,952 A | 9/1950 | Joseph et al. |
| 2,658,368 A | 11/1953 | Siegel |
| 2,782,910 A | 2/1957 | Saul et al. |
| 2,809,634 A | 10/1957 | Hirotada et al. |
| 3,111,396 A | 11/1963 | Ball |
| 3,165,225 A | 1/1965 | Georg et al. |
| 3,402,724 A | 9/1968 | Blount et al. |
| 3,431,393 A | 3/1969 | Katsuda et al. |
| 3,433,632 A | 3/1969 | Elbert et al. |
| 3,490,718 A | 1/1970 | Vary et al. |
| 3,496,336 A | 2/1970 | Hingorany et al. |
| 3,521,643 A | 7/1970 | Toth et al. |
| 3,604,428 A | 9/1971 | Moukaddem |
| 3,722,742 A | 3/1973 | Wertz |
| 3,743,136 A | 7/1973 | Chambers |
| 3,804,100 A | 4/1974 | Fariello |
| 3,861,523 A | 1/1975 | Fountain et al. |
| 3,863,803 A | 2/1975 | Valcic |
| 3,964,902 A | 6/1976 | Fletcher et al. |
| 4,009,713 A | 3/1977 | Simmons et al. |
| 4,031,906 A | 6/1977 | Knapp |
| 4,094,119 A | 6/1978 | Sullivan |
| 4,145,001 A | 3/1979 | Weyenberg et al. |
| 4,161,283 A | 7/1979 | Hyman |
| 4,190,412 A | 2/1980 | Nitta |
| 4,193,513 A | 3/1980 | Bull, Jr. |
| 4,214,658 A | 7/1980 | Crow |
| 4,449,039 A | 5/1984 | Fukazawa et al. |
| 4,503,851 A | 3/1985 | Braunroth |
| D279,508 S | 7/1985 | Bauer et al. |
| 4,588,976 A | 5/1986 | Jaselli |
| 4,676,237 A | 6/1987 | Wood et al. |
| 4,677,992 A | 7/1987 | Bliznak |
| 4,733,794 A | 3/1988 | Kent |
| 4,735,217 A | 4/1988 | Gerth et al. |
| 4,753,383 A | 6/1988 | Focke et al. |
| 4,793,478 A | 12/1988 | Tudor |
| 4,830,028 A | 5/1989 | Lawson et al. |
| 4,848,374 A | 7/1989 | Chard et al. |
| 4,878,832 A | 11/1989 | Lynch |
| 4,885,129 A | 12/1989 | Leonard et al. |
| 4,917,301 A | 4/1990 | Munteanu |
| 4,922,901 A | 5/1990 | Brooks et al. |
| 4,923,052 A | 5/1990 | Englebert |
| 4,923,059 A | 5/1990 | Evers et al. |
| 4,947,874 A | 8/1990 | Brooks et al. |
| 4,947,875 A | 8/1990 | Brooks et al. |
| 4,961,438 A | 10/1990 | Korte |
| 4,978,814 A | 12/1990 | Honour |
| 5,027,837 A | 7/1991 | Clearman et al. |
| 5,044,550 A | 9/1991 | Lamm |
| 5,046,514 A | 9/1991 | Bolt |
| 5,060,671 A | 10/1991 | Counts et al. |
| D322,687 S | 12/1991 | Tschudin |
| 5,095,647 A | 3/1992 | Zobele et al. |
| 5,095,921 A | 3/1992 | Losee et al. |
| 5,096,921 A | 3/1992 | Bollinger et al. |
| 5,099,861 A | 3/1992 | Clearman et al. |
| 5,121,881 A | 6/1992 | Lembeck |
| 5,167,242 A | 12/1992 | Turner et al. |
| 5,179,966 A | 1/1993 | Losee et al. |
| 5,247,947 A | 9/1993 | Clearman et al. |
| 5,269,327 A | 12/1993 | Counts et al. |
| D346,878 S | 5/1994 | Gee et al. |
| 5,322,075 A | 6/1994 | Deevi et al. |
| 5,357,271 A | 10/1994 | Wiklof et al. |
| 5,388,574 A | 2/1995 | Ingebrethsen |
| 5,390,864 A | 2/1995 | Alexander |
| 5,404,890 A | 4/1995 | Gentry et al. |
| 5,408,574 A | 4/1995 | Deevi et al. |
| 5,448,317 A | 9/1995 | Huang |
| 5,479,948 A | 1/1996 | Counts et al. |
| 5,497,792 A | 3/1996 | Prasad et al. |
| 5,501,236 A | 3/1996 | Hill et al. |
| 5,505,214 A | 4/1996 | Collins et al. |
| 5,530,225 A | 6/1996 | Hajaligol |
| 5,540,241 A | 7/1996 | Kim |
| 5,553,791 A | 9/1996 | Alexander |
| 5,568,819 A | 10/1996 | Gentry et al. |
| 5,636,787 A | 6/1997 | Gowhari |
| 5,649,554 A | 7/1997 | Sprinkel et al. |
| 5,659,656 A | 8/1997 | Das |
| 5,666,977 A | 9/1997 | Higgins et al. |
| 5,692,291 A | 12/1997 | Deevi et al. |
| D392,069 S | 3/1998 | Rowland |
| 5,743,251 A | 4/1998 | Howell et al. |
| D404,201 S | 1/1999 | Wennerstrom |
| 5,865,185 A | 2/1999 | Collins et al. |
| 5,875,968 A | 3/1999 | Miller et al. |
| 5,878,722 A | 3/1999 | Gras et al. |
| 5,878,752 A | 3/1999 | Adams et al. |
| 5,896,984 A | 4/1999 | Focke et al. |
| D414,892 S | 10/1999 | Chen |
| 5,967,312 A | 10/1999 | Jacobs |
| 6,040,560 A | 3/2000 | Fleischhauer et al. |
| 6,058,711 A | 5/2000 | Maciaszek et al. |
| 6,065,592 A | 5/2000 | Wik |
| 6,095,505 A | 8/2000 | Miller |
| D432,263 S | 10/2000 | Issa |
| D434,217 S | 11/2000 | Packard et al. |
| D434,979 S | 12/2000 | Liu |
| 6,155,268 A * | 12/2000 | Takeuchi ............. A24F 47/008 131/273 |
| D436,725 S | 1/2001 | Rogers |

(56) References Cited

U.S. PATENT DOCUMENTS

| | | |
|---|---|---|
| D438,003 S | 2/2001 | Minagawa et al. |
| D441,133 S | 4/2001 | Emery |
| 6,275,650 B1 | 8/2001 | Lambert |
| D449,521 S | 10/2001 | Pinkus et al. |
| 6,321,757 B1 | 11/2001 | McCutcheon |
| 6,446,793 B1 | 9/2002 | Layshock |
| D466,012 S | 11/2002 | Baker |
| D470,765 S | 2/2003 | Baker |
| D471,804 S | 3/2003 | Staples |
| D472,012 S | 3/2003 | South |
| 6,527,166 B1 | 3/2003 | Focke et al. |
| 6,530,495 B1 | 3/2003 | Joseph |
| 6,561,391 B1 | 5/2003 | Baker |
| 6,652,804 B1 | 11/2003 | Neumann et al. |
| 6,681,998 B2 | 1/2004 | Sharpe et al. |
| 6,701,921 B2 | 3/2004 | Sprinkel, Jr. et al. |
| 6,715,605 B1 | 4/2004 | Manservigi et al. |
| D493,617 S | 8/2004 | Armato |
| 6,790,496 B1 | 9/2004 | Levander et al. |
| 6,830,046 B2 | 12/2004 | Blakley et al. |
| D509,732 S | 9/2005 | Staples |
| 7,100,618 B2 | 9/2006 | Dominguez |
| 7,112,712 B1 | 9/2006 | Ancell |
| D545,186 S | 6/2007 | Liebe et al. |
| D549,573 S | 8/2007 | Liebe et al. |
| 7,253,282 B2 | 8/2007 | Dehmlow et al. |
| 7,263,228 B2 | 8/2007 | Mori |
| 7,263,282 B2 | 8/2007 | Meyer |
| D550,455 S | 9/2007 | Barnhart |
| D566,329 S | 4/2008 | Bagaric et al. |
| D566,890 S | 4/2008 | Bagaric et al. |
| 7,389,878 B1 | 6/2008 | Torrico |
| D573,889 S | 7/2008 | Short et al. |
| 7,400,940 B2 | 7/2008 | McRae et al. |
| D575,451 S | 8/2008 | Jones et al. |
| 7,455,176 B2 | 11/2008 | Focke et al. |
| 7,540,286 B2 | 6/2009 | Cross et al. |
| 7,565,969 B2 | 7/2009 | He |
| D606,854 S | 12/2009 | Greenhalgh |
| D610,983 S | 3/2010 | Wai |
| D611,806 S | 3/2010 | Bried |
| D613,903 S | 4/2010 | Wu et al. |
| D613,904 S | 4/2010 | Wu et al. |
| D616,753 S | 6/2010 | Beam et al. |
| 7,767,698 B2 | 8/2010 | Warchol et al. |
| 7,832,410 B2 | 11/2010 | Hon |
| D628,469 S | 12/2010 | Taylor et al. |
| D631,838 S | 2/2011 | Cheng |
| D636,257 S | 4/2011 | Bougoulas et al. |
| 7,992,554 B2 | 8/2011 | Radomski et al. |
| D649,658 S | 11/2011 | Belfance et al. |
| D650,738 S | 12/2011 | Leung |
| 8,113,343 B2 | 2/2012 | Åkerlind et al. |
| D656,094 S | 3/2012 | Wu |
| 8,156,944 B2 | 4/2012 | Han |
| D661,016 S | 5/2012 | Borges et al. |
| D671,677 S | 11/2012 | Wu |
| D671,678 S | 11/2012 | Wu |
| 8,307,834 B1 | 11/2012 | Palmerino, Sr. et al. |
| D672,642 S | 12/2012 | Supranowicz |
| D674,539 S | 1/2013 | Wu |
| 8,365,742 B2 | 2/2013 | Hon |
| 8,375,957 B2 | 2/2013 | Hon |
| 8,393,331 B2 | 3/2013 | Hon |
| 8,430,106 B2 | 4/2013 | Potter et al. |
| 8,448,783 B2 | 5/2013 | Vecchi |
| 8,490,628 B2 | 7/2013 | Hon |
| 8,511,318 B2 | 8/2013 | Hon |
| D693,055 S | 11/2013 | Manca et al. |
| D700,397 S | 2/2014 | Manca et al. |
| 8,689,805 B2 | 4/2014 | Hon |
| 8,752,545 B2 | 6/2014 | Buchberger |
| 8,794,245 B1 | 8/2014 | Scatterday |
| 8,833,364 B2 | 9/2014 | Buchberger |
| D715,760 S | 10/2014 | Kim et al. |
| D716,267 S | 10/2014 | Kim et al. |
| 8,869,793 B1 | 10/2014 | Spandorfer et al. |
| 8,910,640 B2 | 12/2014 | Sears et al. |
| D720,884 S | 1/2015 | Liu |
| 8,948,578 B2 | 2/2015 | Buchberger |
| D723,738 S | 3/2015 | Liu |
| 8,967,155 B2 | 3/2015 | Bundren et al. |
| 9,055,617 B2 | 6/2015 | Thorens et al. |
| D736,460 S | 8/2015 | McKeon et al. |
| D737,507 S | 8/2015 | Liu |
| 9,609,894 B2 | 4/2017 | Abramov et al. |
| 9,623,205 B2 | 4/2017 | Buchberger |
| 9,730,276 B2 | 8/2017 | Vissa et al. |
| 9,943,108 B2 | 4/2018 | Lord |
| 9,961,939 B2 | 5/2018 | Reevell |
| 9,974,335 B2 | 5/2018 | Lord |
| 9,986,760 B2 | 6/2018 | Macko et al. |
| 10,010,695 B2 | 7/2018 | Buchberger |
| 10,045,562 B2 | 8/2018 | Buchberger |
| 10,278,421 B2 | 5/2019 | Lord |
| 10,368,582 B2 | 8/2019 | Lord |
| 2001/0004934 A1 | 6/2001 | Yamamoto et al. |
| 2001/0042546 A1 | 11/2001 | Umeda et al. |
| 2002/0005207 A1 | 1/2002 | Wrenn et al. |
| 2002/0016370 A1 | 2/2002 | Shytle et al. |
| 2002/0079309 A1 | 6/2002 | Cox et al. |
| 2003/0005620 A1 | 1/2003 | Ananth et al. |
| 2003/0049025 A1 | 3/2003 | Neumann et al. |
| 2003/0056791 A1 | 3/2003 | Nichols et al. |
| 2003/0064340 A1 | 4/2003 | Pappas |
| 2003/0079309 A1 | 5/2003 | Vandenbelt et al. |
| 2003/0106552 A1 | 6/2003 | Sprinkel, Jr. et al. |
| 2003/0108342 A1 | 6/2003 | Sherwood et al. |
| 2003/0108743 A1 | 6/2003 | Anderson |
| 2003/0168057 A1 | 9/2003 | Snyder et al. |
| 2003/0200964 A1 | 10/2003 | Blakley et al. |
| 2003/0202169 A1 | 10/2003 | Liu |
| 2004/0031485 A1 | 2/2004 | Rustad et al. |
| 2004/0056651 A1 | 3/2004 | Marietta Bersana |
| 2004/0129793 A1 | 7/2004 | Nguyen et al. |
| 2004/0210151 A1 | 10/2004 | Tsukashima et al. |
| 2004/0226568 A1 | 11/2004 | Takeuchi et al. |
| 2005/0063686 A1 | 3/2005 | Whittle et al. |
| 2005/0087460 A1 | 4/2005 | Bruhn et al. |
| 2005/0145260 A1 | 7/2005 | Inagaki et al. |
| 2005/0194013 A1 | 9/2005 | Wright |
| 2005/0204799 A1 | 9/2005 | Koch |
| 2005/0211243 A1 | 9/2005 | Esser |
| 2005/0224375 A1 | 10/2005 | Focke et al. |
| 2005/0235991 A1 | 10/2005 | Nichols et al. |
| 2005/0268911 A1 | 12/2005 | Cross et al. |
| 2006/0018840 A1 | 1/2006 | Lechuga-Ballesteros et al. |
| 2006/0078477 A1 | 4/2006 | Althouse et al. |
| 2006/0095311 A1 | 5/2006 | Thompson |
| 2006/0137681 A1 | 6/2006 | Von Hollen et al. |
| 2006/0180143 A1 | 8/2006 | Lind et al. |
| 2006/0196518 A1 | 9/2006 | Hon |
| 2006/0283468 A1 | 12/2006 | Lipowicz |
| 2007/0014549 A1 | 1/2007 | Demarest et al. |
| 2007/0045288 A1 | 3/2007 | Nelson |
| 2007/0062548 A1 | 3/2007 | Horstmann et al. |
| 2007/0102013 A1 | 5/2007 | Adams et al. |
| 2007/0107879 A1 | 5/2007 | Radomski et al. |
| 2007/0144514 A1 | 6/2007 | Yeates et al. |
| 2007/0155255 A1 | 7/2007 | Galauner et al. |
| 2007/0193895 A1 | 8/2007 | Weiss et al. |
| 2007/0267031 A1 | 11/2007 | Hon |
| 2007/0267032 A1 | 11/2007 | Shan |
| 2008/0017204 A1 | 1/2008 | Braunshteyn et al. |
| 2008/0092912 A1 | 4/2008 | Robinson et al. |
| 2008/0156326 A1 | 7/2008 | Belcastro et al. |
| 2008/0216828 A1 | 9/2008 | Wensley et al. |
| 2008/0223382 A1 | 9/2008 | Zeanah |
| 2008/0241255 A1 | 10/2008 | Rose et al. |
| 2009/0090472 A1 | 4/2009 | Radomski |
| 2009/0095311 A1 | 4/2009 | Han |
| 2009/0095312 A1 | 4/2009 | Herbrich et al. |
| 2009/0188490 A1 | 7/2009 | Han |

(56) References Cited

U.S. PATENT DOCUMENTS

| | | |
|---|---|---|
| 2009/0220222 A1* | 9/2009 | Rabin .................... F04B 19/24 392/396 |
| 2009/0241947 A1 | 10/2009 | Bedini et al. |
| 2009/0266837 A1 | 10/2009 | Gelardi et al. |
| 2009/0272379 A1 | 11/2009 | Thorens et al. |
| 2009/0288966 A1 | 11/2009 | Minarelli et al. |
| 2009/0293892 A1 | 12/2009 | Williams et al. |
| 2009/0324206 A1 | 12/2009 | Young et al. |
| 2010/0003904 A1 | 1/2010 | Duescher |
| 2010/0006113 A1 | 1/2010 | Urtsev et al. |
| 2010/0059070 A1 | 3/2010 | Potter et al. |
| 2010/0065653 A1 | 3/2010 | Wingo et al. |
| 2010/0083959 A1 | 4/2010 | Siller |
| 2010/0108059 A1 | 5/2010 | Axelsson et al. |
| 2010/0181387 A1 | 7/2010 | Zaffaroni et al. |
| 2010/0182608 A1 | 7/2010 | Zribi et al. |
| 2010/0211011 A1 | 8/2010 | Haar |
| 2010/0236546 A1 | 9/2010 | Yamada et al. |
| 2010/0242974 A1 | 9/2010 | Pan |
| 2010/0313901 A1 | 12/2010 | Fernando et al. |
| 2011/0011396 A1 | 1/2011 | Fang |
| 2011/0036363 A1 | 2/2011 | Urtsev et al. |
| 2011/0094523 A1 | 4/2011 | Thorens et al. |
| 2011/0126848 A1 | 6/2011 | Zuber et al. |
| 2011/0155153 A1 | 6/2011 | Thorens et al. |
| 2011/0155718 A1 | 6/2011 | Greim et al. |
| 2011/0180433 A1 | 7/2011 | Rennecamp |
| 2011/0192914 A1 | 8/2011 | Ishigami |
| 2011/0209717 A1 | 9/2011 | Han |
| 2011/0226236 A1* | 9/2011 | Buchberger ...... A61M 15/0086 128/200.23 |
| 2011/0277757 A1 | 11/2011 | Terry |
| 2011/0278189 A1 | 11/2011 | Terry |
| 2011/0290267 A1 | 12/2011 | Yamada et al. |
| 2011/0297166 A1 | 12/2011 | Takeuchi et al. |
| 2011/0303231 A1* | 12/2011 | Li ........................ A24F 47/008 131/329 |
| 2011/0309157 A1 | 12/2011 | Yang et al. |
| 2012/0111347 A1 | 5/2012 | Hon |
| 2012/0145169 A1 | 6/2012 | Wu |
| 2012/0180994 A1 | 7/2012 | Yang et al. |
| 2012/0180995 A1 | 7/2012 | Yang et al. |
| 2012/0199146 A1 | 8/2012 | Marangos |
| 2012/0227752 A1 | 9/2012 | Alelov |
| 2012/0227753 A1 | 9/2012 | Newton |
| 2012/0242974 A1 | 9/2012 | LaValley et al. |
| 2012/0255567 A1 | 10/2012 | Rose et al. |
| 2012/0260927 A1 | 10/2012 | Liu |
| 2012/0285476 A1 | 11/2012 | Hon |
| 2013/0074857 A1 | 3/2013 | Buchberger |
| 2013/0081623 A1 | 4/2013 | Buchberger |
| 2013/0087160 A1 | 4/2013 | Gherghe |
| 2013/0098786 A1 | 4/2013 | Collins |
| 2013/0112214 A1 | 5/2013 | Bundren et al. |
| 2013/0142782 A1 | 6/2013 | Rahmel et al. |
| 2013/0192615 A1 | 8/2013 | Tucker et al. |
| 2013/0192619 A1 | 8/2013 | Tucker et al. |
| 2013/0192621 A1 | 8/2013 | Li et al. |
| 2013/0192623 A1 | 8/2013 | Tucker et al. |
| 2013/0213419 A1 | 8/2013 | Tucker et al. |
| 2013/0228191 A1* | 9/2013 | Newton ................ A24F 47/008 131/329 |
| 2013/0255702 A1 | 10/2013 | Griffith, Jr. et al. |
| 2013/0284192 A1 | 10/2013 | Peleg et al. |
| 2013/0306084 A1 | 11/2013 | Flick |
| 2013/0319407 A1 | 12/2013 | Liu |
| 2013/0333700 A1 | 12/2013 | Buchberger |
| 2013/0340779 A1 | 12/2013 | Liu |
| 2013/0341218 A1 | 12/2013 | Liu |
| 2013/0342157 A1 | 12/2013 | Liu |
| 2014/0000638 A1 | 1/2014 | Sebastian et al. |
| 2014/0007863 A1 | 1/2014 | Chen |
| 2014/0007892 A1 | 1/2014 | Liu |
| 2014/0020697 A1 | 1/2014 | Liu |
| 2014/0048086 A1 | 2/2014 | Zhanghua |
| 2014/0053831 A1 | 2/2014 | Leamon et al. |
| 2014/0060528 A1 | 3/2014 | Liu |
| 2014/0060554 A1 | 3/2014 | Collett et al. |
| 2014/0060555 A1 | 3/2014 | Chang et al. |
| 2014/0064715 A1 | 3/2014 | Greim et al. |
| 2014/0106155 A1 | 4/2014 | Iandoli Espinosa |
| 2014/0123989 A1 | 5/2014 | LaMothe |
| 2014/0182608 A1 | 7/2014 | Egoyants et al. |
| 2014/0196717 A1 | 7/2014 | Liu |
| 2014/0196731 A1 | 7/2014 | Scatterday |
| 2014/0202454 A1 | 7/2014 | Buchberger |
| 2014/0202476 A1 | 7/2014 | Egoyants et al. |
| 2014/0209105 A1 | 7/2014 | Sears et al. |
| 2014/0216485 A1 | 8/2014 | Petr et al. |
| 2014/0238396 A1 | 8/2014 | Buchberger |
| 2014/0238423 A1 | 8/2014 | Tucker et al. |
| 2014/0238424 A1 | 8/2014 | Macko et al. |
| 2014/0261490 A1 | 9/2014 | Kane |
| 2014/0261495 A1 | 9/2014 | Novak, III et al. |
| 2014/0270726 A1 | 9/2014 | Egoyants et al. |
| 2014/0270730 A1 | 9/2014 | DePiano et al. |
| 2014/0283825 A1 | 9/2014 | Buchberger |
| 2014/0286630 A1 | 9/2014 | Buchberger |
| 2014/0299125 A1 | 10/2014 | Buchberger |
| 2014/0305431 A1 | 10/2014 | Holley et al. |
| 2014/0332019 A1 | 11/2014 | Liu |
| 2014/0338680 A1 | 11/2014 | Abramov et al. |
| 2015/0114411 A1 | 4/2015 | Buchberger |
| 2015/0128964 A1 | 5/2015 | Bundren et al. |
| 2015/0128971 A1 | 5/2015 | Verleur et al. |
| 2015/0136756 A1 | 5/2015 | Vissa et al. |
| 2015/0157055 A1 | 6/2015 | Christopher |
| 2015/0181934 A1 | 7/2015 | Lyubomirskiy et al. |
| 2015/0181937 A1 | 7/2015 | Dubief et al. |
| 2015/0196058 A1 | 7/2015 | Lord |
| 2015/0201675 A1 | 7/2015 | Lord |
| 2015/0208728 A1 | 7/2015 | Lord |
| 2016/0073693 A1 | 3/2016 | Reevell |
| 2016/0101909 A1 | 4/2016 | Schennum et al. |
| 2016/0106154 A1 | 4/2016 | Lord |
| 2016/0106155 A1 | 4/2016 | Reevell |
| 2016/0120218 A1 | 5/2016 | Schennum et al. |
| 2016/0278163 A1 | 9/2016 | Chen |
| 2016/0353804 A1 | 12/2016 | Lord |
| 2017/0006916 A1 | 1/2017 | Liu |
| 2017/0027225 A1 | 2/2017 | Helmut et al. |
| 2017/0042245 A1 | 2/2017 | Buchberger et al. |
| 2017/0188629 A1 | 7/2017 | Dickens et al. |
| 2017/0188630 A1 | 7/2017 | Buchberger |
| 2017/0197043 A1 | 7/2017 | Helmut |
| 2017/0197044 A1 | 7/2017 | Helmut |
| 2017/0197046 A1 | 7/2017 | Helmut |
| 2018/0192705 A1 | 7/2018 | Lord |
| 2018/0235284 A1 | 8/2018 | Lord |
| 2019/0254350 A1 | 8/2019 | Christopher |
| 2019/0289920 A1 | 9/2019 | Christopher |

FOREIGN PATENT DOCUMENTS

| | | |
|---|---|---|
| AT | 507188 A4 | 3/2010 |
| AT | 508244 A4 | 12/2010 |
| AT | 510405 A4 | 4/2012 |
| AT | 510504 A1 | 4/2012 |
| AU | 6391373 A | 6/1975 |
| AU | 6393173 A | 6/1975 |
| BR | 6402132 U | 7/1986 |
| CA | 2309376 A1 | 11/2000 |
| CA | 2824970 A1 | 8/2012 |
| CH | 698603 B1 | 9/2009 |
| CL | 199400288 A1 | 8/1995 |
| CL | 199900377 | 3/1999 |
| CN | 2092880 U | 1/1992 |
| CN | 2220168 Y | 2/1996 |
| CN | 1126425 A | 7/1996 |
| CN | 1205849 A | 1/1999 |
| CN | 1312730 A | 9/2001 |
| CN | 1329567 A | 1/2002 |
| CN | 1333657 A | 1/2002 |
| CN | 2485265 Y | 4/2002 |

(56) References Cited

FOREIGN PATENT DOCUMENTS

| | | |
|---|---|---|
| CN | 2660914 Y | 12/2004 |
| CN | 1607911 A | 4/2005 |
| CN | 2719043 Y | 8/2005 |
| CN | 1694765 A | 11/2005 |
| CN | 1703279 A | 11/2005 |
| CN | 1286409 C | 11/2006 |
| CN | 2904674 Y | 5/2007 |
| CN | 200966824 Y | 10/2007 |
| CN | 101115901 A | 1/2008 |
| CN | 201023852 Y | 2/2008 |
| CN | 201238609 Y | 5/2009 |
| CN | 201240612 Y | 5/2009 |
| CN | 201375023 Y | 1/2010 |
| CN | 101648041 A | 2/2010 |
| CN | 201430913 Y | 3/2010 |
| CN | 101843368 A | 9/2010 |
| CN | 201592850 U | 9/2010 |
| CN | 101878958 A | 11/2010 |
| CN | 101925309 A | 12/2010 |
| CN | 201657770 U | 12/2010 |
| CN | 102014677 A | 4/2011 |
| CN | 201830900 U | 5/2011 |
| CN | 201860753 U | 6/2011 |
| CN | 102264249 A | 11/2011 |
| CN | 102264420 A | 11/2011 |
| CN | 102326869 A | 1/2012 |
| CN | 202122096 U | 1/2012 |
| CN | 102389166 A | 3/2012 |
| CN | 202172846 U | 3/2012 |
| CN | 102655773 A | 9/2012 |
| CN | 202722498 U | 2/2013 |
| CN | 202750708 U | 2/2013 |
| CN | 103052380 A | 4/2013 |
| CN | 103960782 A | 8/2014 |
| CN | 203986095 U | 12/2014 |
| CN | 204048047 U | 12/2014 |
| CN | 104602553 A | 5/2015 |
| CN | 204317492 U | 5/2015 |
| CN | 104684422 A | 6/2015 |
| CN | 204598339 U | 8/2015 |
| CN | 104983079 A | 10/2015 |
| CN | 105310114 A | 2/2016 |
| CN | 105394816 A | 3/2016 |
| CN | 205106385 U | 3/2016 |
| CN | 106102863 A | 11/2016 |
| DE | 594585 | 3/1934 |
| DE | 2653133 A1 | 5/1978 |
| DE | 2940797 A1 | 4/1981 |
| DE | 3148335 A1 | 7/1983 |
| DE | 3218760 A1 | 12/1983 |
| DE | 3936687 A1 | 5/1990 |
| DE | 29719509 U1 | 1/1998 |
| DE | 19630619 A1 | 2/1998 |
| DE | 19654945 A1 | 3/1998 |
| DE | 10330681 B3 | 6/2004 |
| DE | 202006013439 U1 | 10/2006 |
| DE | 202013100606 U1 | 2/2013 |
| EA | 019736 B1 | 5/2014 |
| EA | 022685 B1 | 2/2016 |
| EP | 0280262 A2 | 8/1988 |
| EP | 0295122 A2 | 12/1988 |
| EP | 0358002 A2 | 3/1990 |
| EP | 0358114 A2 | 3/1990 |
| EP | 0444553 A2 | 9/1991 |
| EP | 0488488 A1 | 6/1992 |
| EP | 0845220 A1 | 6/1998 |
| EP | 0847220 A2 | 6/1998 |
| EP | 0893071 A1 | 1/1999 |
| EP | 0893171 A1 | 1/1999 |
| EP | 1166814 A2 | 1/2002 |
| EP | 1166847 A2 | 1/2002 |
| EP | 1468618 A1 | 10/2004 |
| EP | 1736065 A1 | 12/2006 |
| EP | 1757921 A2 | 2/2007 |
| EP | 1772166 A1 | 4/2007 |
| EP | 1820748 A1 | 8/2007 |
| EP | 1847671 A1 | 10/2007 |
| EP | 1950439 A1 | 7/2008 |
| EP | 2018886 A1 | 1/2009 |
| EP | 2022349 A1 | 2/2009 |
| EP | 2022350 A1 | 2/2009 |
| EP | 2113178 A1 | 11/2009 |
| EP | 2234891 A2 | 10/2010 |
| EP | 2340729 A1 | 7/2011 |
| EP | 2358418 A1 | 8/2011 |
| EP | 2404515 A1 | 1/2012 |
| EP | 2468116 A1 | 6/2012 |
| EP | 2468118 A1 | 6/2012 |
| EP | 2698070 A1 | 2/2014 |
| EP | 2762019 A1 | 8/2014 |
| EP | 2785208 A1 | 10/2014 |
| EP | 2801273 A2 | 11/2014 |
| EP | 2835062 A1 | 2/2015 |
| EP | 2871985 A1 | 5/2015 |
| EP | 2907397 A1 | 8/2015 |
| EP | 2907397 B1 | 9/2017 |
| EP | 3117860 B1 | 1/2019 |
| FR | 472030 A | 11/1914 |
| FR | 960469 A | 4/1950 |
| FR | 1292446 A | 5/1962 |
| GB | 190930472 | 12/1909 |
| GB | 191100628 A | 11/1911 |
| GB | 25575 A | 3/1912 |
| GB | 191311086 A | 9/1913 |
| GB | 110216 A | 10/1917 |
| GB | 111454 A | 11/1917 |
| GB | 120016 A | 10/1918 |
| GB | 160493 A | 3/1921 |
| GB | 163124 A | 5/1921 |
| GB | 215992 A | 5/1924 |
| GB | 220229 A | 8/1924 |
| GB | 268967 A | 4/1927 |
| GB | 402064 A | 11/1933 |
| GB | 507955 A | 6/1939 |
| GB | 544329 A | 4/1942 |
| GB | 565574 A | 11/1944 |
| GB | 611596 A | 11/1948 |
| GB | 626888 A | 7/1949 |
| GB | 871869 A | 7/1961 |
| GB | 1313525 A | 4/1973 |
| GB | 1046183 | 7/1988 |
| GB | 2275464 A | 8/1994 |
| GB | 2068034 | 11/1997 |
| GB | 2369108 A | 5/2002 |
| GB | 4000273 | 12/2006 |
| GB | 4006615 | 10/2008 |
| GB | 2504075 A | 1/2014 |
| GB | 2513635 A | 11/2014 |
| HK | 1196511 A | 10/2016 |
| HK | 1226611 | 10/2017 |
| JP | S5289386 A | 7/1977 |
| JP | S5752456 A | 3/1982 |
| JP | S57140354 A | 8/1982 |
| JP | S59106340 A | 6/1984 |
| JP | S6121542 B2 | 5/1986 |
| JP | S6196763 A | 5/1986 |
| JP | S6196765 A | 5/1986 |
| JP | H01117775 A | 5/1989 |
| JP | H02124081 A | 5/1990 |
| JP | H02124082 A | 5/1990 |
| JP | H0548944 A | 2/1993 |
| JP | H05103836 A | 4/1993 |
| JP | H05309136 A | 11/1993 |
| JP | 3003543 U | 10/1994 |
| JP | H06303837 A | 11/1994 |
| JP | H06315366 A | 11/1994 |
| JP | H07147965 A | 6/1995 |
| JP | H08299862 A | 11/1996 |
| JP | H08511176 A | 11/1996 |
| JP | H1189551 A | 4/1999 |
| JP | H11503912 A | 4/1999 |
| JP | H11514018 A | 11/1999 |
| JP | H11514081 A | 11/1999 |
| JP | 3003543 B2 | 1/2000 |

(56) References Cited

FOREIGN PATENT DOCUMENTS

| | | |
|---|---|---|
| JP | 2001502542 A | 2/2001 |
| JP | 2001248842 A | 9/2001 |
| JP | 2002527153 A | 8/2002 |
| JP | 3093201 U | 4/2003 |
| JP | 2003226577 A | 8/2003 |
| JP | 2004097617 A | 4/2004 |
| JP | 2004332069 A | 11/2004 |
| JP | 2005013092 A | 1/2005 |
| JP | 2005138773 A | 6/2005 |
| JP | 2005524067 A | 8/2005 |
| JP | 2005537918 A | 12/2005 |
| JP | 2005537919 A | 12/2005 |
| JP | 2005538149 A | 12/2005 |
| JP | 2005538159 A | 12/2005 |
| JP | 2007057532 A | 3/2007 |
| JP | 2007097787 A | 4/2007 |
| JP | 2007512880 A | 5/2007 |
| JP | 2007297124 A | 11/2007 |
| JP | 2008544834 A | 12/2008 |
| JP | 2009509523 A | 3/2009 |
| JP | 2009526714 A | 7/2009 |
| JP | 2009529871 A | 8/2009 |
| JP | 2009537119 A | 10/2009 |
| JP | 2010080261 A | 4/2010 |
| JP | 2011087569 A | 5/2011 |
| JP | 2011515093 A | 5/2011 |
| JP | 2011518567 A | 6/2011 |
| JP | 2012013247 A | 1/2012 |
| JP | 2012026933 A | 2/2012 |
| JP | 2012029633 A | 2/2012 |
| JP | 2012057859 A | 3/2012 |
| JP | 2012506263 A | 3/2012 |
| JP | 2012249854 A | 12/2012 |
| JP | 2014501107 A | 1/2014 |
| JP | 2014511175 A | 5/2014 |
| JP | 2014524313 A | 9/2014 |
| JP | 2014525251 A | 9/2014 |
| JP | 2015505476 A | 2/2015 |
| JP | 2015513970 A | 5/2015 |
| JP | 2015521847 A | 8/2015 |
| KR | 920017172 A | 9/1992 |
| KR | 100244670 B1 | 2/2000 |
| KR | 20050037919 A | 4/2005 |
| KR | 20100006995 U | 7/2010 |
| KR | 20110006928 U | 7/2011 |
| KR | 20120025569 A | 3/2012 |
| KR | 20120070731 A | 7/2012 |
| KR | 20130004985 A | 1/2013 |
| KR | 20130006714 A | 1/2013 |
| KR | 20130006714 U | 11/2013 |
| KR | 200470732 Y1 | 1/2014 |
| KR | 20140128449 A | 11/2014 |
| NL | 6617184 A | 6/1967 |
| RU | 2311859 C2 | 12/2007 |
| RU | 2328192 C1 | 7/2008 |
| RU | 2336001 C2 | 10/2008 |
| RU | 2360583 C1 | 7/2009 |
| RU | 89927 U1 | 12/2009 |
| RU | 94815 U1 | 6/2010 |
| RU | 103281 U1 | 4/2011 |
| RU | 115629 U1 | 5/2012 |
| RU | 121706 U1 | 11/2012 |
| RU | 122000 U1 | 11/2012 |
| RU | 124120 U1 | 1/2013 |
| RU | 132318 U1 | 9/2013 |
| RU | 2509516 C2 | 3/2014 |
| UA | 89752 C2 | 3/2010 |
| UA | 67598 U | 2/2012 |
| UA | 78167 U | 3/2013 |
| WO | WO-9527412 A1 | 10/1995 |
| WO | WO-9632854 A2 | 10/1996 |
| WO | WO-9748293 A1 | 12/1997 |
| WO | WO-9817131 A1 | 4/1998 |
| WO | WO-0009188 A1 | 2/2000 |
| WO | WO-0021598 A1 | 4/2000 |
| WO | WO-0028842 A1 | 5/2000 |
| WO | WO-0050111 A1 | 8/2000 |
| WO | WO-02051468 A2 | 7/2002 |
| WO | WO-02058747 A1 | 8/2002 |
| WO | WO-02060769 A1 | 8/2002 |
| WO | WO-03005045 A1 | 1/2003 |
| WO | WO-03028409 A1 | 4/2003 |
| WO | WO-03050405 A1 | 6/2003 |
| WO | WO-03083283 A1 | 10/2003 |
| WO | WO-03101454 A1 | 12/2003 |
| WO | WO-2004022128 A2 | 3/2004 |
| WO | WO-2004022242 A1 | 3/2004 |
| WO | WO-2004022243 A1 | 3/2004 |
| WO | WO-2005106350 A2 | 11/2005 |
| WO | WO-2006082571 A1 | 8/2006 |
| WO | WO-2007040941 A1 | 4/2007 |
| WO | WO-2007042941 A2 | 4/2007 |
| WO | WO-2007108877 A2 | 9/2007 |
| WO | WO-2007131448 A1 | 11/2007 |
| WO | WO-2007131449 A1 | 11/2007 |
| WO | WO-2007141668 A2 | 12/2007 |
| WO | WO-2008006048 A2 | 1/2008 |
| WO | WO-2008038144 A2 | 4/2008 |
| WO | WO-2008104870 A1 | 9/2008 |
| WO | WO-2009001085 A2 | 12/2008 |
| WO | WO-2009015410 A1 | 2/2009 |
| WO | WO-2009092862 A1 | 7/2009 |
| WO | WO-2009092419 A3 | 9/2009 |
| WO | WO-2009118085 A1 | 10/2009 |
| WO | WO-2009132793 A1 | 11/2009 |
| WO | WO-2010045670 A1 | 4/2010 |
| WO | WO-2010045671 A1 * | 4/2010 .......... A61M 11/041 |
| WO | WO-2011050943 A1 | 5/2011 |
| WO | WO-2011050964 A1 | 5/2011 |
| WO | WO-2011079932 A1 | 7/2011 |
| WO | WO-2011109849 A1 | 9/2011 |
| WO | WO-2011137453 A2 | 11/2011 |
| WO | WO-2012025496 A1 | 3/2012 |
| WO | WO-2012065310 A1 | 5/2012 |
| WO | WO-2012065754 A2 | 5/2012 |
| WO | WO-2012085203 A1 | 6/2012 |
| WO | WO-2012085207 A1 | 6/2012 |
| WO | WO-2012106739 A1 | 8/2012 |
| WO | WO-2012114082 A1 | 8/2012 |
| WO | WO-2013013808 A1 | 1/2013 |
| WO | WO-2013025921 A1 | 2/2013 |
| WO | WO-2013034453 A1 | 3/2013 |
| WO | WO-2013034460 A1 | 3/2013 |
| WO | WO-2013045942 A2 | 4/2013 |
| WO | WO-2013057185 A1 | 4/2013 |
| WO | WO-2013082173 A1 | 6/2013 |
| WO | WO-2013083631 A1 | 6/2013 |
| WO | WO-2013098395 A1 | 7/2013 |
| WO | WO-2013116558 A1 | 8/2013 |
| WO | WO-2013116571 A1 | 8/2013 |
| WO | WO-2013116572 A1 | 8/2013 |
| WO | WO-2013142671 A1 | 9/2013 |
| WO | WO-2013152873 A1 | 10/2013 |
| WO | WO-2013178769 A1 | 12/2013 |
| WO | WO-2013189050 A1 | 12/2013 |
| WO | WO-2013189052 A1 | 12/2013 |
| WO | WO-2014005275 A1 | 1/2014 |
| WO | WO-2014012906 A1 | 1/2014 |
| WO | WO-2014015463 A1 | 1/2014 |
| WO | WO-2014061477 A1 | 4/2014 |
| WO | WO-2014071329 A1 | 5/2014 |
| WO | WO-2014130695 A1 | 8/2014 |
| WO | WO-2014140320 A1 | 9/2014 |
| WO | WO-2014150131 A1 | 9/2014 |
| WO | WO-2015114327 A1 | 8/2015 |
| WO | WO-2015114328 A1 | 8/2015 |
| WO | WO-2015165812 A1 | 11/2015 |

OTHER PUBLICATIONS

Application and File History for U.S. Appl. No. 13/125,343, filed Apr. 21, 2011, inventor Buchberger.

(56) References Cited

OTHER PUBLICATIONS

Application and File History for U.S. Appl. No. 13/984,512, filed Aug. 29, 2013, inventor Buchberger.
Application and File History for U.S. Appl. No. 14/235,210, filed Mar. 4, 2014, inventor Buchberger.
Application and File History for U.S. Appl. No. 14/268,909, filed May 2, 2014, inventor Buchberger.
Application and File History for U.S. Appl. No. 14/296,803, filed Jun. 5, 2014, inventor Buchberger.
Application and File History for U.S. Appl. No. 14/306,831, filed Jun. 17, 2014, inventor Buchberger.
Application and File History for U.S. Appl. No. 14/353,256, filed Apr. 21, 2014, inventor Buchberger.
Application and File History for U.S. Appl. No. 14/594,065, filed Jan. 9, 2015, Inventor Buchberger.
Application and File History for U.S. Appl. No. 14/787,946, filed Oct. 29, 2015, inventor Lord.
Application and File History for U.S. Appl. No. 14/888,514, filed Nov. 2, 2015, inventor Reevell.
Application and File History for U.S. Appl. No. 14/888,517, filed Nov. 2, 2015, Inventor Reevell.
Application and File History for U.S. Appl. No. 15/307,095, filed Oct. 27, 2016, inventor Buchberger.
Application and File History for U.S. Appl. No. 15/454,156, filed Mar. 9, 2017, inventor Buchberger.
Application and File History for U.S. Appl. No. 15/470,078, filed Mar. 27, 2017, inventor Buchberger.
Application and File History for U.S. Appl. No. 15/470,089, filed Mar. 27, 2017, inventor Buchberger.
Application and File History for U.S. Appl. No. 15/470,095, filed Mar. 27, 2017, inventor Buchberger.
Application and File History for U.S. Appl. No. 15/997,113, filed Jun. 4, 2018, inventor Buchberger.
Application and File History for U.S. Appl. No. 16/096,554, filed Oct. 25, 2018, Inventor Fraser.
Company Filtrona Richmond Inc., http://www.filtronaporoustechnologies.com, Nov. 19, 2018, 1 page.
Decision on Appeal, U.S. Appl. No. 14/306,831, dated Mar. 26, 2020, 6 pages.
Decision to Grant a Patent dated May 22, 2018 for Japanese Application No. 2016-134648, 5 pages.
Decision to Grant for Great Britain Application No. GB1405720.2, dated Sep. 26, 2017, 2 pages.
Decision to Grant dated Apr. 1, 2014 for Russian Application No. 2011120430, 16 pages.
Decision to Grant dated Aug. 5, 2014 for Japanese Application No. 2011-532464, 6 pages.
Diener Electronic, "Plasma Polymerization," The company Diener electronic GmbH+Co. KG, Retrieved on Oct. 17, 2017, 19 pages.
Dunn P.D., et al., "Heat Pipes," Fourth Edition, Pergamon, ISBN0080419038, 1994, 14 pages.
ECF, "Welcome to the World's Largest E-Cigarette Website: The Voice of Vaping since 2007," Oct. 2011, Nichrome or Kanthal Specs for Purchasing, retrieved on Apr. 19, 2020, 6 pages.
Examination Report for Great Britain Application No. GB1405720.2, dated Jun. 27, 2017, 3 pages.
Examination Report dated Nov. 20 for Australian Application No. 2017256084, 3 pages.
Examination Report dated Dec. 15, 2017, for Australian Application No. 201512626, 3 pages.
Extended European Search Report for Application No. 15178588, dated Apr. 14, 2016, 2 pages.
Extended European Search Report for Application No. 17189951.1, dated Jan. 4, 2018, 11 pages.
Extended European Search Report for Application No. 19196432.9, dated Dec. 9, 2019, 14 pages.
First Office Action for Chinese Application No. 201480031926.5 dated Apr. 21, 2017, 12 pages.
First Office Action dated Dec. 3, 2012 for Chinese Application No. 200980152395.4, 16 pages.

Hegboom T., "Integrating Electrical Heating Elements in Appliance Design," cited in EPO Opposition File Wrapper for EP2871983, resulting in interlocutory decision dated Aug. 7, 2019, 4 pages.
Hong Kong Publication, Application No. 14110165.2, published on Dec. 19, 2014, 1 page.
Hong Kong Publication, Application No. 16113324.2, published on Oct. 6, 2017, 1 page.
Iatty, "An Idea of the Iatty, Welcome to the World's Largest E-Cigarette Website: The Voice of Vaping since 2007," retrieved on Dec. 17, 2019, p. 23, Post 443 and 445, 7 pages.
Iatty, "An Idea of the Iatty, Welcome to the World's Largest E-Cigarette Website: The Voice of Vaping since 2007," retrieved on Dec. 17, 2019, p. 24, Post 467, 6 pages.
Iatty, "An Idea of the Iatty, Welcome to the World's Largest E-Cigarette Website: The Voice of Vaping since 2007," retrieved on Dec. 17, 2019, p. 37, Post 727, 6 pages.
Iatty, "An Idea of the Iatty, Welcome to the World's Largest E-Cigarette Website: The Voice of Vaping since 2007," retrieved on Dec. 17, 2019, Page, Post 1, 7 pages.
"Integrating Electrical Heating Elements in Product Design," Metallic Resistance Heating Wire, Chapter 1, Section 1.1 to 1.3.2 cited in EPO Opposition File Wrapper for EP2871983, resulting in interlocutory decision dated Aug. 7, 2019, 6 pages.
"Integrating Electrical Heating Elements in Product Design," Metallic Resistance Heating Wire, Chapter 1, Section 1.4 cited in EPO Opposition File Wrapper for EP2871983, resulting in interlocutory decision dated Aug. 7, 2019, 1 page.
"Integrating Electrical Heating Elements in Product Design," Metallic Resistance Heating Wire, cited in EPO Opposition File Wrapper for EP2871983, resulting in interlocutory decision dated Aug. 7, 2019, 8 pages.
International Preliminary Report on Patentability for Application No. PCT/AT2012/000017, dated Aug. 13, 2013, 5 pages.
International Preliminary Report on Patentability for Application No. PCT/EP2012/070647, dated Apr. 22, 2014, 8 pages.
International Preliminary Report on Patentability for Application No. PCT/GB2014/051332, dated Nov. 12, 2015, 7 pages.
International Preliminary Report on Patentability for Application No. PCT/GB2014/051333, dated Aug. 5, 2015, 12 pages.
International Preliminary Report on Patentability for Application No. PCT/GB2014/051334, dated Nov. 12, 2015, 7 pages.
International Preliminary Report on Patentability for Application No. PCT/GB2014/051688, dated Dec. 17, 2015, 6 pages.
International Preliminary Report on Patentability for Application No. PCT/GB2015/050195, dated May 13, 2016, 17 pages.
International Preliminary Report on Patentability for Application No. PCT/GB2015/051213, dated Jul. 14, 2016, 20 pages.
International Preliminary Report on Patentability for Application No. PCT/GB2015/053445, dated Jan. 24, 2017, 19 pages.
International Preliminary Report on Patentability for Application No. PCT/GB2017/051139, dated Aug. 6, 2018, 7 pages.
International Preliminary Report on Patentability dated Sep. 9, 2014 for Application No. PCT/EP2013/64922, filed Jul. 15, 2013, 10 pages.
International Search Report and Written Opinion for Application No. PCT/AT2012/000017, dated Jul. 3, 2012, 6 pages.
International Search Report and Written Opinion for Application No. PCT/EP2012/003103, dated Nov. 26, 2012, 6 pages.
International Search Report and Written Opinion for Application No. PCT/EP2012/070647, dated Feb. 6, 2013, 9 pages.
International Search Report and Written Opinion for Application No. PCT/GB2014/051332, dated Jul. 21, 2014, 8 pages.
International Search Report and Written Opinion for Application No. PCT/GB2014/051333, dated Jul. 17, 2014, 10 pages.
International Search Report and Written Opinion for Application No. PCT/GB2014/051334, dated Jul. 21, 2014, 8 pages.
International Search Report and Written Opinion for Application No. PCT/GB2015/053445, dated Apr. 18, 2016, 21 pages.
International Search Report and Written Opinion for Application No. PCT/GB2017/051139, dated Aug. 9, 2017, 14 pages.
International Search Report and Written Opinion dated Oct. 11, 2013 for Application No. PCT/EP2013/064922, filed Jul. 15, 2013, 6 pages.

(56) References Cited

OTHER PUBLICATIONS

International Search Report for App No. PCT/GB2015/050195, dated Sep. 2, 2015, 4 pages.
International Search Report for Application No. PCT/AT2009/000413, dated Jan. 25, 2010, 3 pages.
International Search Report for Application No. PCT/AT2009/000414, dated Jan. 26, 2010, 2 pages.
International Search Report for Application No. PCT/GB2014/051633, dated Dec. 4, 2014, 7 pages.
International Search Report for Application No. PCT/GB2014/051688, dated Aug. 26, 2014, 4 pages.
International Search Report for Application No. PCT/GB2015/051213, dated Jul. 16, 2015, 5 pages.
Kynol, "Standard Specifications of Kynol™ Activated Carbon Fiber Products," Sep. 19, 2013, 2 pages.
Iatty, "E-Cigarette Forum," p. 10, May 2011, commentary by Imeothanasis and Iorderos33, retrieved on Feb. 11, 2019, 8 pages.
Notice of Allowance dated Oct. 18, 2019 for Korean Application No. 1020167018457, 2 pages (with translation—3 pages).
Notice of Allowance dated May 30, 2017 for Korean Application No. 1020157001277, 4 pages (No translation available).
Notice of Allowance dated Jun. 27, 2018 for Korean Application No. 1020167020977, 3 pages.
Notice of Opposition Letter from EPO Opposition against the European Application No. 2358418, dated Mar. 1, 2017, 60 pages.
Notice of Opposition dated Oct. 30, 2019 for European Application No. 16166656.5, 39 pages.
Notice of Reasons for Rejection dated Oct. 15, 2013 for Japanese Application No. 2011532464, 6 pages.
Notice of Reasons for Rejection dated May 23, 2017 for Japanese Application No. 2016134648, 18 pages.
Notice of Reasons for Rejection dated May 31, 2016 for Japanese Application No. 2015-137361, 6 pages.
Notice of Reasons for Rejection dated Oct. 7, 2013 for Japanese Application No. 2011532464, 6 pages.
Notice of Reasons for Rejection dated Sep. 8, 2015 for Japanese Application No. 2014179732, 5 pages.
Notice of Reasons for Revocation dated Apr. 17, 2017 for Japanese Patent No. 5960358, with English translation, 12 pages.
Notification of Transmittal of IPRP for International Application No. PCT/GB2014/051633 dated Oct. 23, 2015, 9 pages.
Notification to Grant Patent Right for Invention dated Oct. 25, 2018 for Chinese Application No. 201610086101.4, 2 pages.
Office Action and Search Report dated Feb. 28, 2019 for Japanese Application No. 2018-088088, 25 pages.
Office Action dated Sep. 3, 2014, for Russian Application No. 2013504605, 7 pages.
Office Action dated Jul. 2, 2020 for Chinese Application No. 201780020023.0 filed Sep. 25, 2018, 22 pages.
Office Action dated Nov. 21, 2017 for Russian Application No. 2016142584, 8 pages.
Office Action dated Nov. 22, 2016 for Canadian Application No. 2878951, 3 pages.
Office Action dated Nov. 23, 2018 for Korean Application No. 1020167018457, 6 pages (12 pages with translation).
Office Action dated Apr. 25, 2017 for Japanese Application No. 2016123816, 2 pages (No translation available).
Office Action dated May 12, 2017 for Korean Application No. 10-20157034538, 10 pages.
Office Action for European Application No. 16166656, dated Jul. 29, 2020, 7 pages.
Office Action for Chinese Application No. 201480031296.1 dated Mar. 27, 2017, 13 pages.
Office Action dated Jun. 2, 2016 for Chinese Application No. 201380038075.2, 7 pages (with translation—19 pages).
Office Action dated Sep. 11, 2017 for Chinese Application No. 201480024988.3, 10 pages.
Office Action dated Dec. 12, 2018 for Korean Application No. 10-2017-7015164, 3 pages.
Office Action dated Jun. 15, 2018 for Korean Application No. 10-2017-7015164, 13 pages.
Office Action dated Mar. 16, 2020 for Chinese Patent Application No. 201610255788.X, filed Oct. 21, 2009, 21 pages.
Office Action dated Jan. 18, 2017 for Chinese Application No. 201480024978.X, 8 pages.
Office Action dated Jul. 18, 2018 for Chinese Application No. 201580022356.8, 15 pages.
Office Action dated Sep. 22, 2017 for Russian Application No. 2014120213, 11 pages.
Office Action dated Jan. 25, 2019 for European Application No. 17189951.1, 4 pages.
Office Action dated Jun. 26, 2018 for Japanese Application No. 2017-530762, 16 pages.
Office Action dated Oct. 26, 2016 for Russian Application No. 2014120213, 7 pages.
Office Action dated Sep. 27, 2019 for Korean Application No. 10-20197005785, 13 pages.
Office Action dated Dec. 30, 2016 for Chinese Application No. 201480024988.3, 26 pages.
Office Action dated Sep. 30, 2018 for Chinese Application No. 201610371843.1, 8 pages.
Office Action dated May 4, 2018 for Chinese Application No. 201610086101.4, 7 pages.
Office Action dated Dec. 5, 2017 for Japanese Application No. 2016-564977, 6 pages.
Office Action dated Apr. 10, 2019, for Korean Application No. 1020167018457, 13 pages.
Office Action dated Apr. 23, 2018 for Chinese Application No. 201580006377.0, 9 pages (20 pages with translation).
Office Action dated Dec. 8, 2017, for Korean Application No. 1020167020977, 13 pages.
Office Action dated Jan. 23, 2018, for Japanese Application No. 2016548373,3 pages, (6 pages with translation).
Office Action dated Jun. 5, 2018, for Chinese Application No. 201610552323.0, 11 pages, (18 pages with translation).
Office Action dated Mar. 14, 2018, for Russian Application No. 2016131333, 7 pages (13 pages with translation).
Partial EPO Opposition File Wrapper for EP2871983, resulting in interlocutory decision dated Aug. 7, 2019, 75 pages.
Rudolph G., "The Influence of CO2 on the Sensory Characteristics of the Favor-System," 1987, Accessed at http://legacy.library.ucsf.edu/tid/sld5fl00, 24 pages.
Search Report for Japanese Application No. 2011532464, dated Sep. 18, 2013, 116 pages.
Search Report for Japanese Application No. 2014-179732, dated Sep. 9, 2015, 12 pages.
Search Report for Japanese Application No. 2016134648, dated Mar. 28, 2017, 29 pages.
Search Report for Japanese Application No. 2016-564977, dated Oct. 25, 2017, 19 pages.
Search Report for Japanese Application No. 2011532464, dated Sep. 24, 2013, 53 pages.
Search Report dated Feb. 1, 2017 for Japanese Application No. 2016517671, 13 pages.
Search Report dated Apr. 14, 2017 for Japanese Application No. 2016-134648, 31 pages.
Search Report dated Sep. 19, 2013 for Japanese Application No. 2011-532464, 116 pages.
Search Report dated Apr. 24, 2017 for Russian Application No. 2015146843, 3 pages.
Search Report dated Apr. 25, 2018 for Chinese Application No. 201610086101.4, 1 page.
Search Report dated Aug. 25, 2015 for Japanese Application No. 2014-179732, 10 pages.
Search Report dated Oct. 25, 2017 for Japanese Application No. 2016-864977, 19 pages.
Search Report dated May 29, 2015 for Great Britain Application No. 1422018, 3 pages.
Search Report dated Mar. 20, 2015, for Great Britain Application No. GB1401520.0, 2 pages.
Second Office Action dated Aug. 20, 2013 for Chinese Application No. 200980152395.4, 16 pages.

(56) References Cited

OTHER PUBLICATIONS

Sharafat et al., "Ceramic Foams: Inspiring New Solid Breeder Materials," 12th International Workshop on Ceramic Breeder Blanket Interactions, Germany, Sep. 16-17, 2004, 22 pages.
Supulveda et al., "Processing of Cellular Ceramics by Foaming and In Situ Polymerisation of Organic Monomers," Loughborough University, 1999, 22 pages.
Wires.co.uk, "Bare Nickel Chrome/Nichrome Section," Jun. 20, 2012, 33 pages.
Wires.co.uk, "Specialist in Craft Wire," Jun. 20, 2012, 5 pages.
Written Opinion for Application No. PCT/AT2009/000413, dated Jan. 25, 2010, 5 pages.
Written Opinion for Application No. PCT/AT2009/000414, dated Jan. 26, 2010, 14 pages.
Written Opinion for Application No. PCT/AT2012/000017, dated Jul. 3, 2012, 4 pages.
Written Opinion for Application No. PCT/GB2014/051633, dated Dec. 4, 2014, 11 pages.
Written Opinion for Application No. PCT/GB2014/051688, dated Aug. 26, 2014, 4 pages.
Written Opinion for Application No. PCT/GB2015/051213, dated Jul. 16, 2015, 9 pages.
Written Opinion dated Jun. 23, 2014 for Application No. PCT/EP2013/064922, filed Jul. 15, 2013, 4 pages.
Written Opinion of the International Preliminary Examining Authority for Application No. PCT/GB2015/050195 dated Jan. 20, 2016, 8 pages.
Written Opinion of the International Searching Authority for Application No. PCT/GB2015/050195, dated Sep. 2, 2015, 8 pages.
Decision to Grant dated Feb. 5, 2018 for Ukraine Application No. 201607243, 6 pages.
Decision to Grant dated Apr. 11, 2016 for Russian Application No. 2015100321, 8 pages (No. translation available).
Decision to Grant dated Jun. 23, 2016 for Ukrainian Application No. 201500198, 6 pages (No. translation available).
Decision to Grant dated Apr. 27, 2017 for Russian Application No. 2015146845, 8 pages.
Decision to Grant for Australian Application No. 2017105898, dated Mar. 16, 2018, 12 pages.
Decision to Grant for Russian Application No. 120267, dated Oct. 26, 2016, 7 pages.
Extended European Search Report for U.S. Appl. No. 15/178,588, dated Apr. 14, 2016, 2 pages.
Extended European Search Report for Application No. 16/166,656, dated Oct. 11, 2016, 9 pages.
Extended European Search Report for Application No. 18205608.5, dated Jul. 12, 2019, 7 pages.
Extended European Search Report for Application No. EP17197150.5, dated Mar. 1, 2018, 6 pages.
Extended European Search Report for Application No. 16151458.3, dated Jul. 11, 2016, 8 pages.
Extended European Search Report for European Application No. 15178588, dated Apr. 22, 2016, 4 pages.
International Preliminary Report on Patentability for Application No. PCT/AT2009/000413, dated May 5, 2011, 7 pages.
International Preliminary Report on Patentability for Application No. PCT/AT2009/000414, dated Apr. 26, 2011, 7 pages.
International Preliminary Report on Patentability for Application No. PCT/EP2012/003103, dated Feb. 6, 2014, 7 pages.
Notice of Reasons for Rejection for Japanese Application No. 2020-121265, dated Jul. 20, 2021, 8 pages.
Office Action dated Sep. 22, 2017 for Russian Application No. 2015146847, 11 pages.
Office Action for Chilean Application No. 201701486 dated Nov. 11, 2019, 10 pages.
Office Action For Chinese Application No. 201780020023.0, dated Mar. 8, 2021, 19 pages.
Office Action dated Nov. 26, 2019 for Brazilian Application No. 112015000872, 4 pages.
Opposition Statement dated Mar. 30, 2017 for Japanese Patent No. 5960358, 144 pages (No. translation available).
Search Report for Chilean Application No. 2019-11665, dated Nov. 11, 2019, 10 pages.
Search Report dated Jun. 24, 2019 for Russian Application No. 2018137583, 2 pages.
Search Report dated Apr. 29, 2019 for Russian Application No. 2018137501, 12 pages.

\* cited by examiner

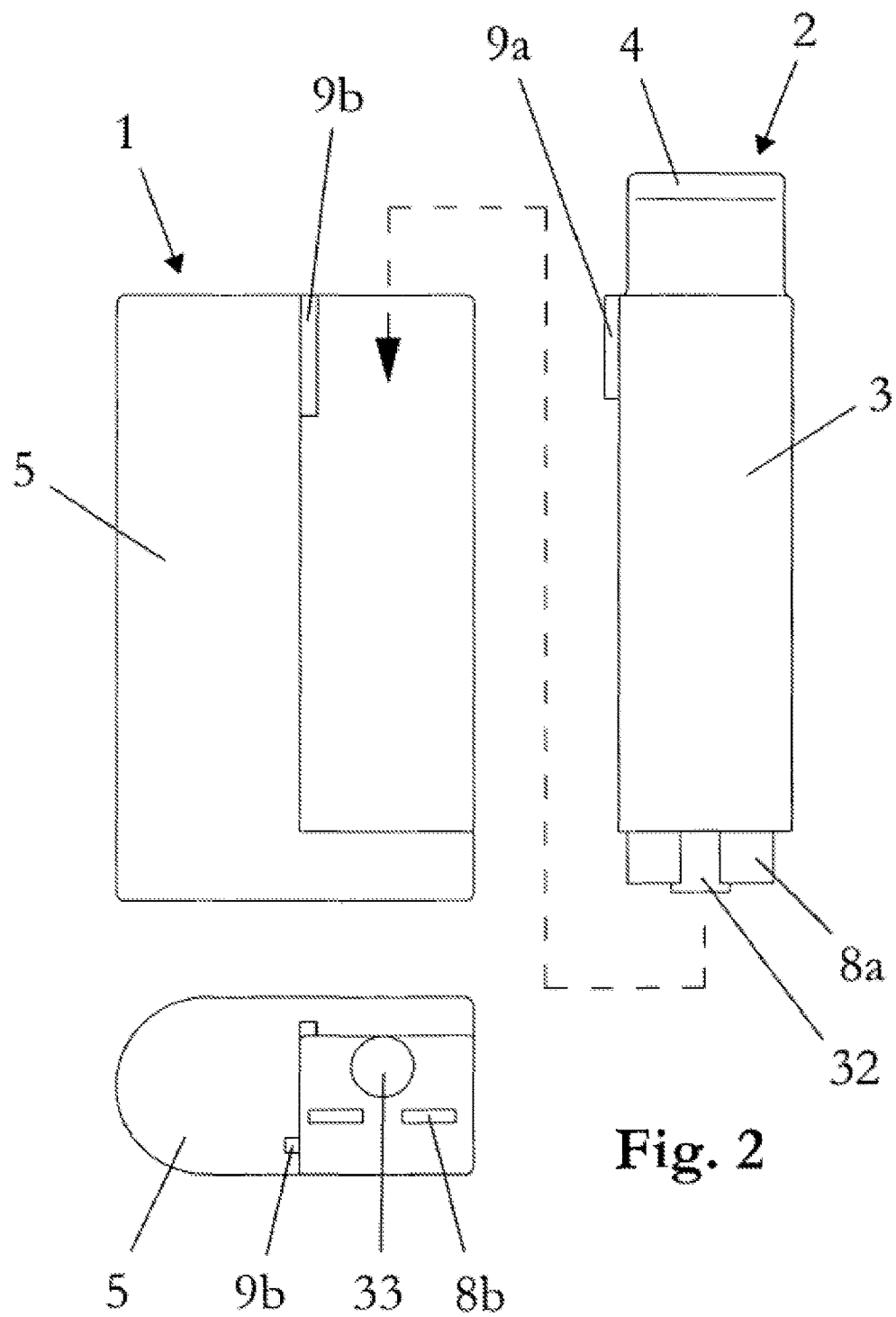

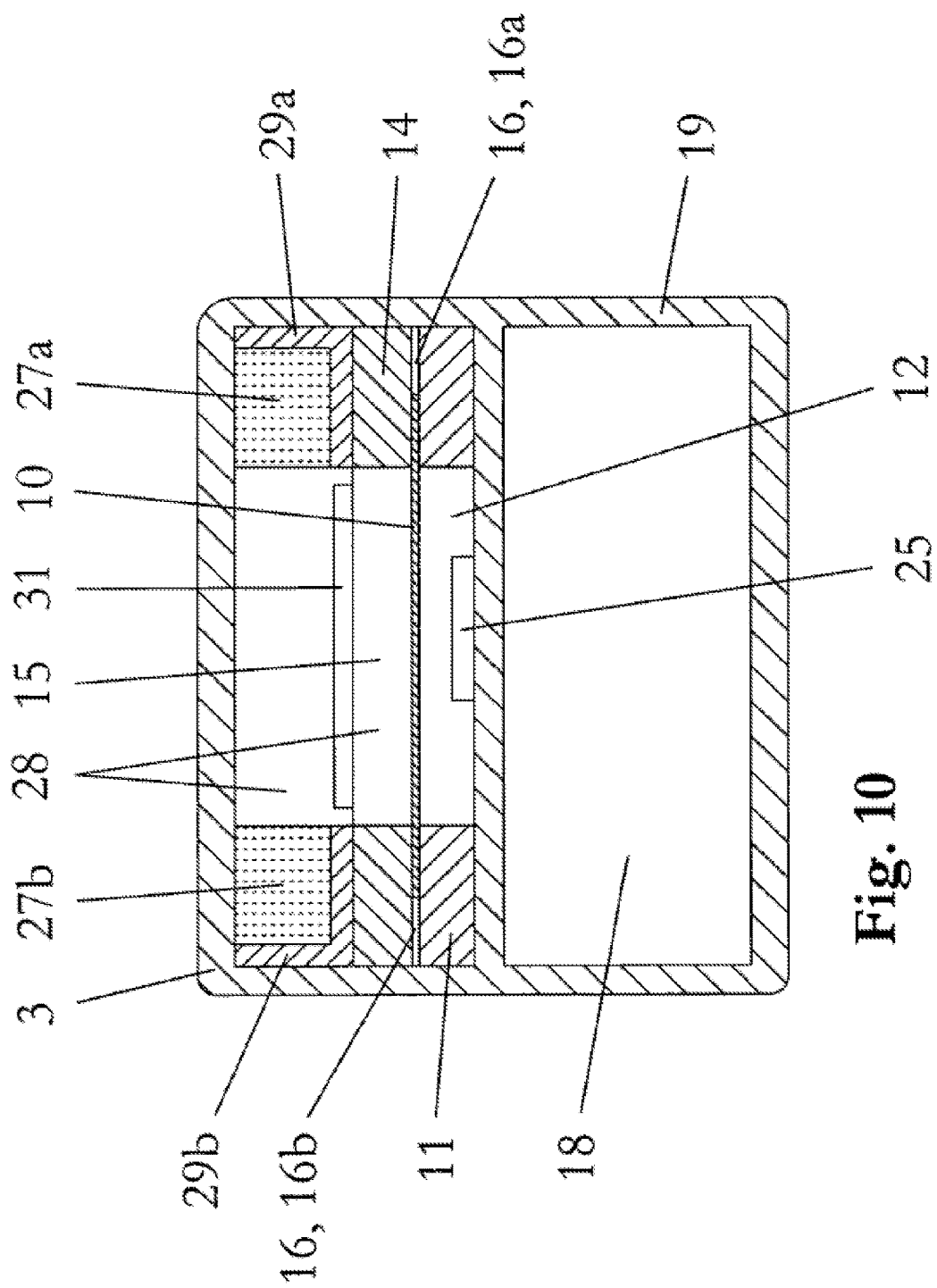

INHALER COMPONENT

RELATED APPLICATION

This application is a continuation of application Ser. No. 14/235,210 filed Mar. 4, 2014, which in turn is a National Phase entry of PCT Application No. PCT/EP2012/003103 filed Jul. 24, 2012, which claims the benefit of AT Application No. A 1095/2011 filed Jul. 27, 2011, each of which is hereby fully incorporated herein by reference.

TECHNICAL FIELD

The invention concerns an inhaler component for forming a vapor/air mixture and/or condensation aerosol by evaporation of a liquid material and optionally condensation of the formed vapor, comprising: an electric heating element for evaporating a portion of the liquid material; a wick with a capillary structure, which wick forms a composite with the heating element and automatically supplies the heating element with the liquid material; a carrier plate, preferably a printed circuit board, which carries the composite and on which the heating element is electrically contacted; a capillary gap formed at least partly by the carrier plate, for the automatic supplying of the composite with the liquid material, while one end portion of the wick extends into the capillary gap; a liquid container containing the liquid material, from which the capillary gap draws the liquid material.

DEFINITION OF TERMS

In the present patent application, the term "inhaler" pertains to medical and nonmedical inhalers. Moreover, the term pertains to inhalers for the administering of pharmaceuticals and substances which have not been declared to be pharmaceuticals. The term furthermore pertains to smoking articles and cigarette replacement articles, such as are contained in European patent class A24F47/00B, insofar as these are intended to provide the user with a vapor/air mixture and/or a condensation aerosol. Nor should the term "inhaler" be subjected to any limitations in regard to how the formed vapor/air mixture and/or condensation aerosol is supplied to the user or his body. The vapor/air mixture and/or condensation aerosol can be inhaled into the lungs, but also supplied only to the oral cavity—without inhalation into the lungs.

By "capillary gap" is meant any gap which brings about a transport of liquid solely by virtue of the capillary effect of its boundary walls. Wicks, jacketed wicks, or channels filled with wick material are not capillary gaps.

The use of the singular "composite" does not exclude the presence of several composites. The invention explicitly includes arrangements with several composites.

BACKGROUND

WO 2010/045671 (Helmut Buchberger) specifies an inhaler component for the intermittent, inhalation-synchronized or draught-synchronized formation of a vapor/air mixture and/or condensation aerosol, consisting of (FIGS. 9-12 and FIGS. 17-18) a housing 3, a chamber 21 arranged in the housing 3, an air inlet opening 26 for the supply of air from the surroundings into the chamber 21, an electric heating element for evaporating a portion of a liquid material 16, wherein the formed vapor mixes in the chamber 21 with the air taken in through the air inlet opening 26, and the vapor/air mixture and/or condensation aerosol is formed.

The inhaler component further comprises a wick with a capillary structure, which wick forms a sheetlike composite 22 with the heating element and automatically resupplies the heating element with the liquid material 16 after an evaporation. The sheetlike composite 22 rests by two end segments on two electrically conducting platelike contacts 23, on whose surface the heating element is electrically contacted at the same time. The platelike contacts can alternatively be formed also by printed circuit boards or a shared printed circuit board. At least one heated section of the sheetlike composite 22 is arranged in the chamber 21 contact-free, and the capillary structure of the wick lies largely free in said section at least on one side 24 of the sheetlike composite. The sheetlike composite 22 or its wick extends by one end into a capillary gap 41, which for its part is or can be capillary coupled to a liquid container 4 containing the liquid material 16. The liquid container 4 has a closure 18 which can be opened and which is still closed before use. The closure 18 can be opened manually by a user, whereupon the liquid material 16 floods a reservoir 45 and wets the capillary gap 41. The capillary gap 41 draws the liquid material 16 out from the liquid container 4 or reservoir 45 and transports it to the composite 22. The capillary gap 41 is formed essentially by one of the two platelike contacts 23 and a top part 42 which is placed on them in a sheetlike manner. Furthermore, a vent channel 52 is fashioned in the platelike contact 23, which connects the reservoir 45 or the liquid container 4 to the chamber 21. The vent channel 52 brings about a pressure equalization, in that each portion of liquid material 16 getting into the capillary gap 41 is replaced immediately by an equal volume of air.

The liquid container 4 in the view according to FIG. 9 is arranged above the platelike contacts 23 carrying the composite 22. This arrangement proves to be definitely space-consuming and means that the dimensions of the inhaler component are relatively large. A further drawback is the fact that the capillary gap 41 is very limited in its surface coverage, inasmuch as a partial vacuum occurs when the capillary gap is in the vertical position due to the weight of the liquid column in the reservoir 45 that is acting on it, which needs to be compensated by the capillarity of the vent channel 52. But if the capillarity of the vent channel 52 is no longer enough to maintain equilibrium, the entire liquid material 16 in the liquid container 4 is liable to run out through the capillary gap 41. Especially when several composites are arranged next to each other (see FIG. 29), and/or when the wick is supposed to be infiltrated by two end segments that are spaced apart from each other, a correspondingly large surface coverage of the capillary gap 41 is required, which can hardly be realized with the above-described arrangement of WO 2010/045671 on account of the effects pointed out.

SUMMARY

The problem of the invention is to eliminate the above-indicated disadvantages of the arrangement known from the prior art. In particular, the problem of the invention is to configure an inhaler component of the kind described above so that a relatively compact overall arrangement can be accomplished with a correspondingly small structural volume. Moreover, it should also be possible to provide capillary gaps with a larger surface coverage.

The problem is solved by the characterizing features of patent claim 1. Accordingly, it is provided that the capillary gap at least partially covers the liquid container on the outside, in a view perpendicular to the carrier plate. In the sense of the present invention, it also counts as "covering" when yet other components are arranged between the capillary gap and the liquid container. If one considers the fact that the components forming the capillary gap require but little space vertically to the carrier plate, it will be appreciated that the arrangement of the invention can save on structural space.

In one modification of the invention, the composite at least partially covers the liquid container on the outside, in a view perpendicular to the carrier plate. In the sense of the present invention, it also counts as "covering" when yet other components are arranged between the composite and the liquid container. If one considers the fact that the composite is generally a relatively thin structure, it will be clear that this further covering can save on structural space even more.

In one preferred embodiment of the invention, the carrier plate is mounted for at least a section on the liquid container. Thus, the liquid container and the carrier plate are arranged in a stack. It is especially advantageous in terms of design for the liquid container to have essentially the shape of a cuboid, and the carrier plate is mounted for at least a section on one side surface of the cuboid. In this way, the available structural space can be utilized optimally. The carrier plate preferably consists of a printed circuit board, especially a so-called multilayer printed circuit board. In this way, the printed tracks carrying electric heating current to and from can be divided among several layers, so that even very large heating currents can be transported mostly free of loss.

The invention furthermore involves an inhaler comprising an inhaler component according to the invention, as described above. Thus, the inhaler component can also be only one part, especially an interchangeable part, of an inhaler.

BRIEF DESCRIPTION OF THE DRAWINGS

The invention will now be explained more closely by means of a sample embodiment according to the drawings. There are shown:

FIG. 2, the inhaler of FIG. 1 with a reusable inhaler part and an interchangeable inhaler component in the decoupled state;

FIG. 10, a sectional view of the interchangeable inhaler component at the height of the composite along line C-C in FIG. 3b.

DETAILED DESCRIPTION

Figure 1:
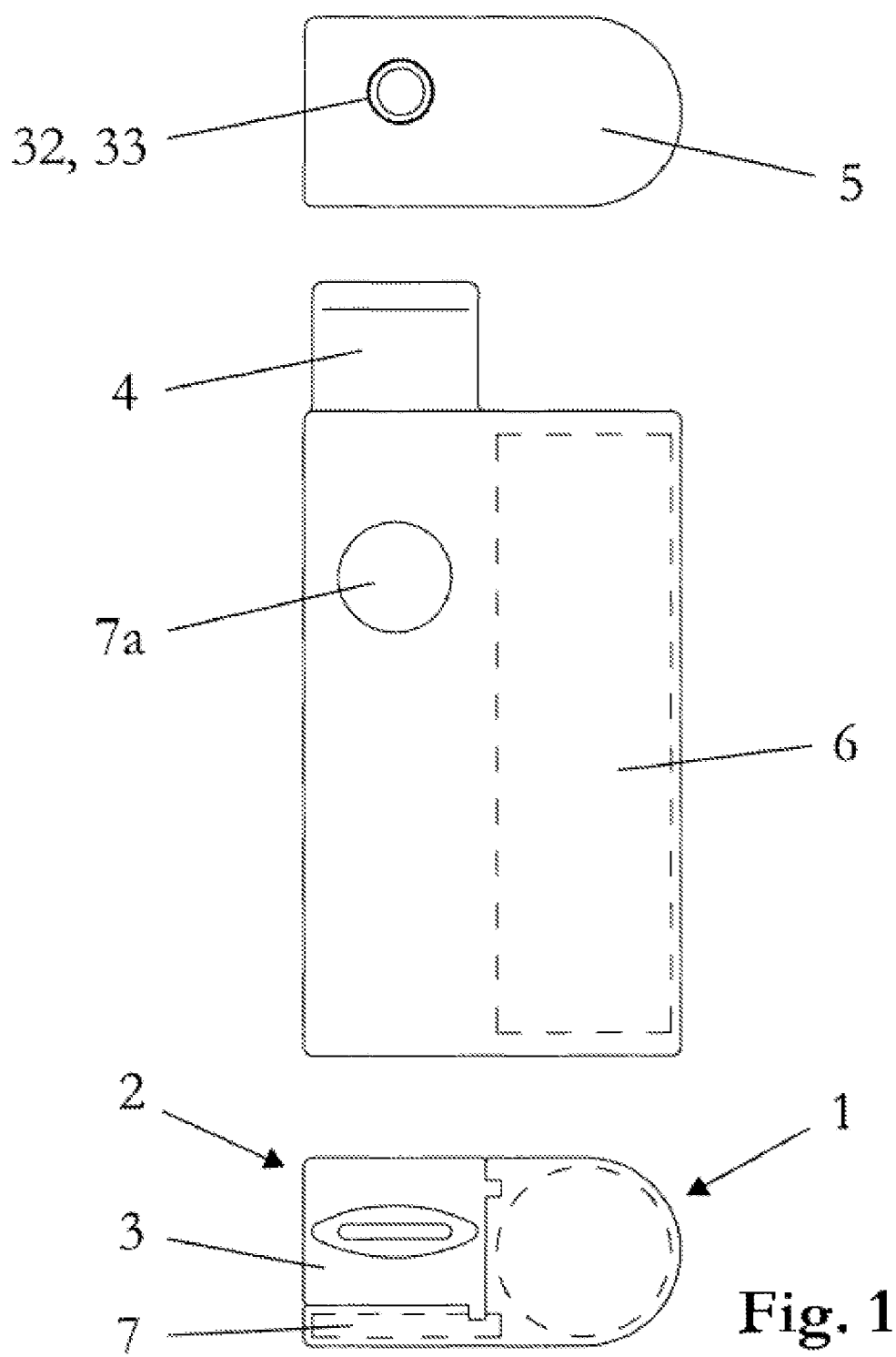
FIG. 1, an inhaler according to the invention in different views.

FIG. 1 shows an inhaler according to the invention, whose shape and size are such that the inhaler can be handled easily and conveniently by users. In terms of volume, the inhaler is only around half the size of a cigarette pack. The example of the inhaler depicted consists essentially of two parts, namely, an inhaler part 1 and an inhaler component 2.

The inhaler component 2 consists of a housing 3, which [has] a mouthpiece 4 similar to a tobacco pipe formed at one end face. The housing 3 is preferably made of plastic. The inhaler component 2 contains a liquid material, which is electrically evaporated inside the housing 3 and converted into an inhalable vapor/air mixture and/or condensation aerosol. The formed vapor/air mixture and/or condensation aerosol is presented to the user through the mouthpiece 4. Essentially, all substances and preparations can be considered as the liquid material that evaporate mostly free of residue under atmospheric conditions This condition is also fulfilled when the particular substance or preparation is present in diluted form, such as dissolved in water and/or ethanol, and the solution evaporates largely free of residue. Thanks to a sufficiently high dilution in an easily volatile solvent such as water and/or ethanol, even hard to evaporate substances can also fulfill the above given condition, and avoid or substantially reduce a thermal decomposition of the liquid material.

The aerosol particles produced by condensation generally have a mass median aerodynamic diameter (MMAD) of less than 2 μm and therefore also reach the alveoli. The inhaler according to the invention is especially suitable for administration of substances with systemic action—especially active substances which display their principal effect in the central nervous system. As an example, one can mention nicotine, whose boiling point is 246 degrees C. The aerosol particles containing nicotine are deposited primarily in the bronchi and alveoli, where the active substance instantly passes into the blood stream. A few seconds later the nicotine reaches the brain in targeted concentration and can display the known effects there.

The inhaler part 1 consists of a main housing 5, which again is preferably made of plastic. The main housing 5 contains at least one battery 6 and an electrical circuit 7 (shown by dotted lines in FIG. 1) with switch 7a. The battery 6 and the electrical circuit 7 provide the necessary electrical energy for the evaporation of the liquid material. The battery 6 preferably consists of a rechargeable battery, such as the type CGR18650K from Panasonic, www.industrial.panasonic.com. This is a cylindrical lithium ion cell of size 18650 with a storage capacity of 1650 mAh and a current capacity up to 30 A. Comparable cells are also manufactured in large numbers by other manufacturers, such as Sony, Samsung, LG Chem.

As shown by FIG. 2, the inhaler part 1 and the inhaler component 2 can be separated from each other in the specific sample embodiment. This arrangement makes the inhaler part 1 reusable, which is basically advisable when one considers that, first, the inhaler part 1 does not come in contact with the liquid material, i.e., it is not contaminated with the liquid material, and second, it contains components which are more long-lived than the parts of the inhaler component 2. The inhaler component 2, after the liquid material has been consumed, is properly disposed of by the user in its entirety and replaced by a new inhaler component 2. Thus, the inhaler component 2 constitutes a disposable, interchangeable article. A proper disposal is especially warranted when the liquid material contains pharmaceuticals or toxins such as nicotine. Essentially, of course, it would also be conceivable to make the inhaler part 1 and the inhaler component 2 as a single piece, i.e., inseparable from each other. However, this embodiment would be less economical, because in this case all parts and components of the inhaler, i.e., the inhaler as a whole, forms a disposable article for onetime use. Of course, the present invention also encompasses this embodiment, and in this case the entire inhaler is to be seen as the inhaler component.

The mechanical coupling between the interchangeable inhaler component 2 and the reusable inhaler part 1 is by insertion tongues 8a and guide tabs 9a formed by the housing 3, which fit into corresponding insert sockets 8b and guide slots 9b formed by the main housing 5 of the reusable inhaler part 1. The insert tongues 8a and insert sockets 8b at the same time serve to channel the electrical energy into the interchangeable inhaler component 2 for evaporation of the liquid material, as will be shown in further detail below.

Figure 3A:
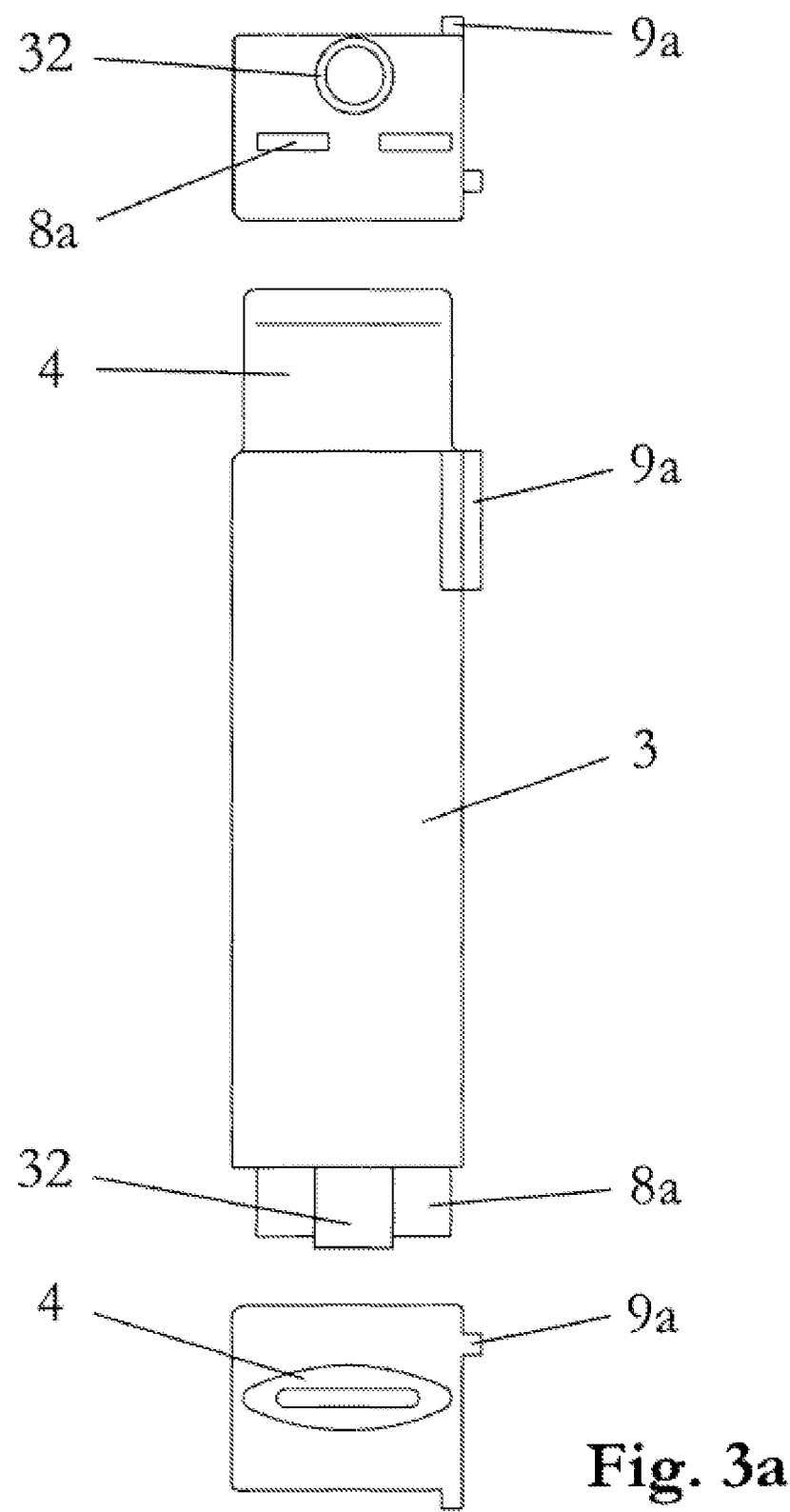
FIGS. 3a and 3b, the interchangeable inhaler component in different views.
Figure 3B:
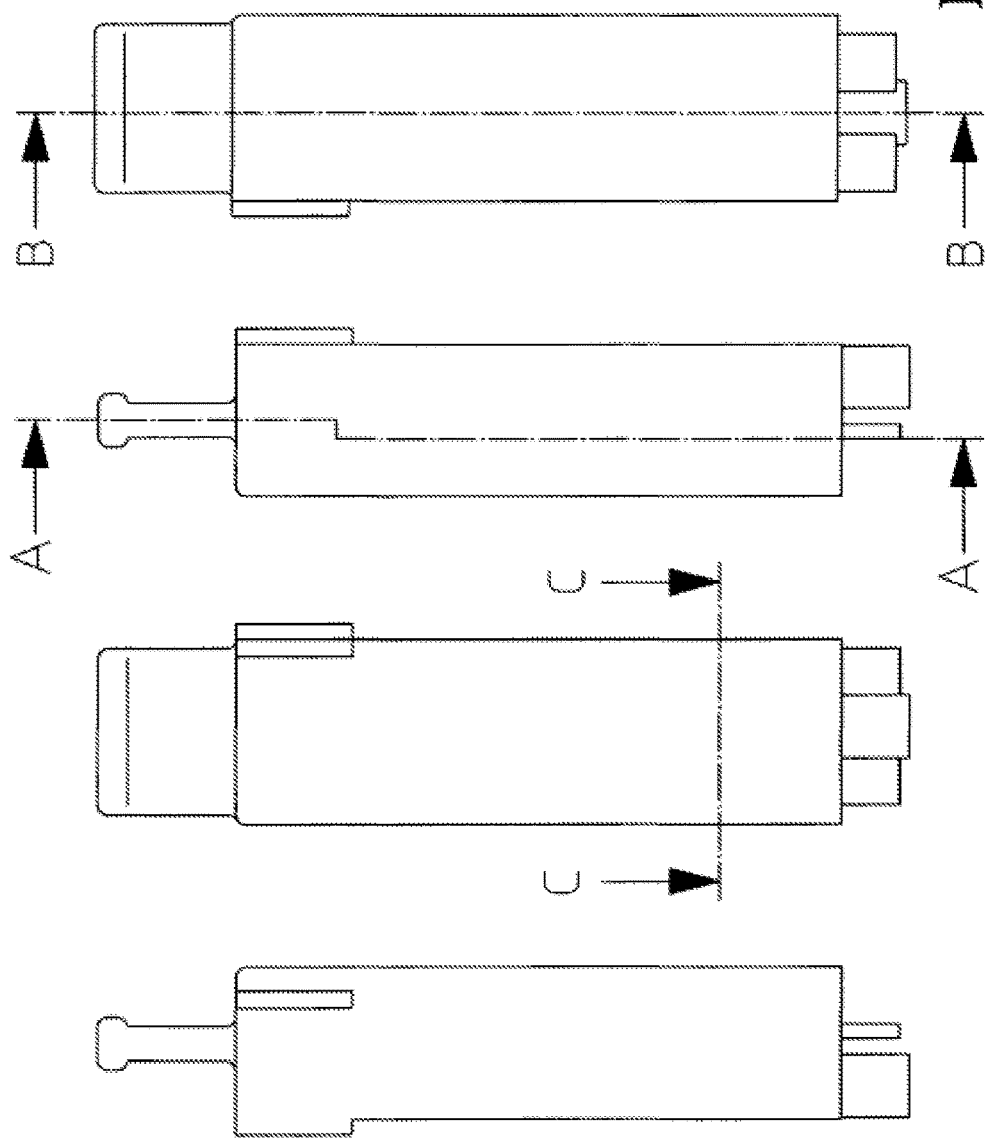

FIGS. 3a and 3b show different views of the interchangeable inhaler component 2. FIGS. 4-9 give further insight into the interior construction of the inhaler component 2. Accordingly, the housing 3 of the inhaler component 2 has an essentially rectangular shape. Inside the rectangular housing 3 are the essential components for forming the vapor/air mixture and/or condensation aerosol. These include in particular the composites 10, which bring about the evaporation of the liquid material. In the specific sample embodiment, there are six composites 10 arranged next to one another, and the composites have a sheetlike shape. The sheetlike composites 10 each consist of a wick and an electrical heating element, which are joined together or integrated in each other in sheetlike manner. For example, the sheetlike composites 10 can be formed by a metal foil and metal weave layers sintered thereupon. Instead of the metal weave, open-pore metal foams can also be used. The open-pore capillary structure of the weave layers sintered on the metal foil or the metal foam form the wick, and the electrical resistance of the metal forms the heating element. Suitable metallic resistance materials are, for example, refined steels such as AISI 304 or AISI 316, as well as heatsealing band alloys, especially NiCr alloys. The manufacture of such sheetlike composites 10 is prior art and is disclosed in detail, for example, in the already cited WO 2010/045671 (Helmut Buchberger).

Figure 4A:
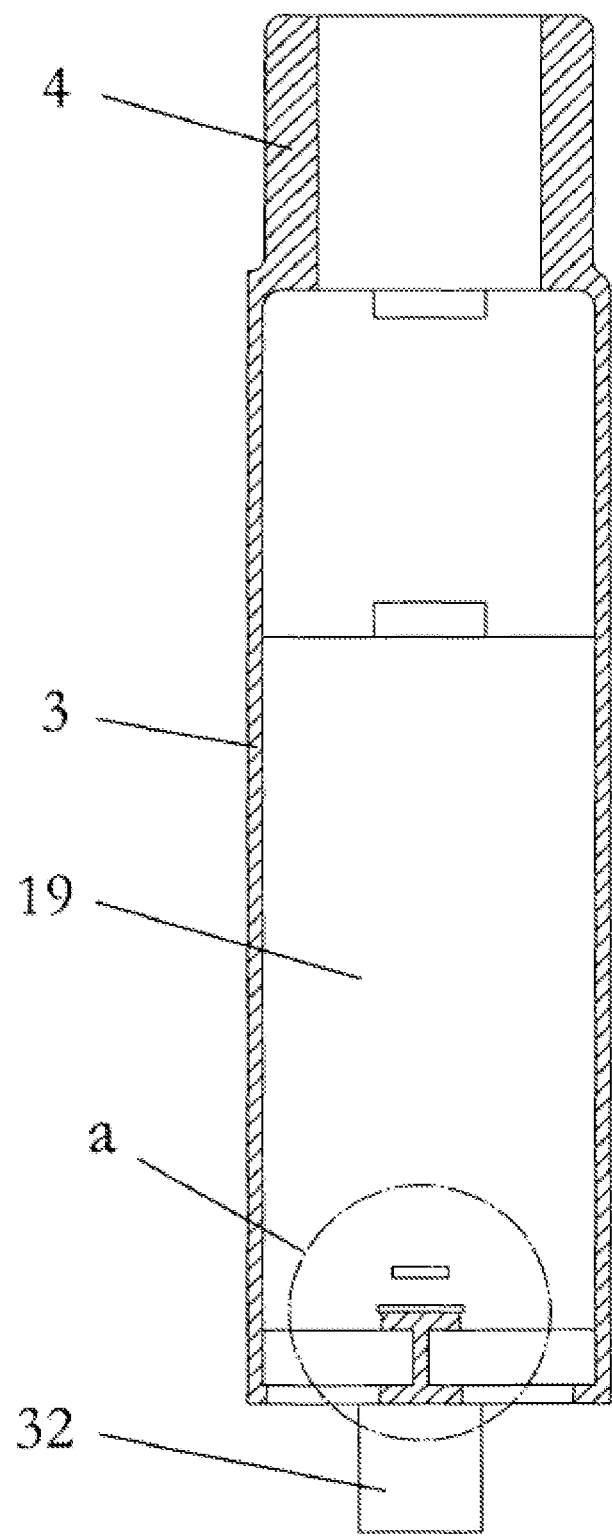
FIGS. 4a, 4b, 4c, 4d and 4e, sectional views of the interchangeable inhaler component along line A-A in FIG. 3b in different assembly states.
Figure 4B:
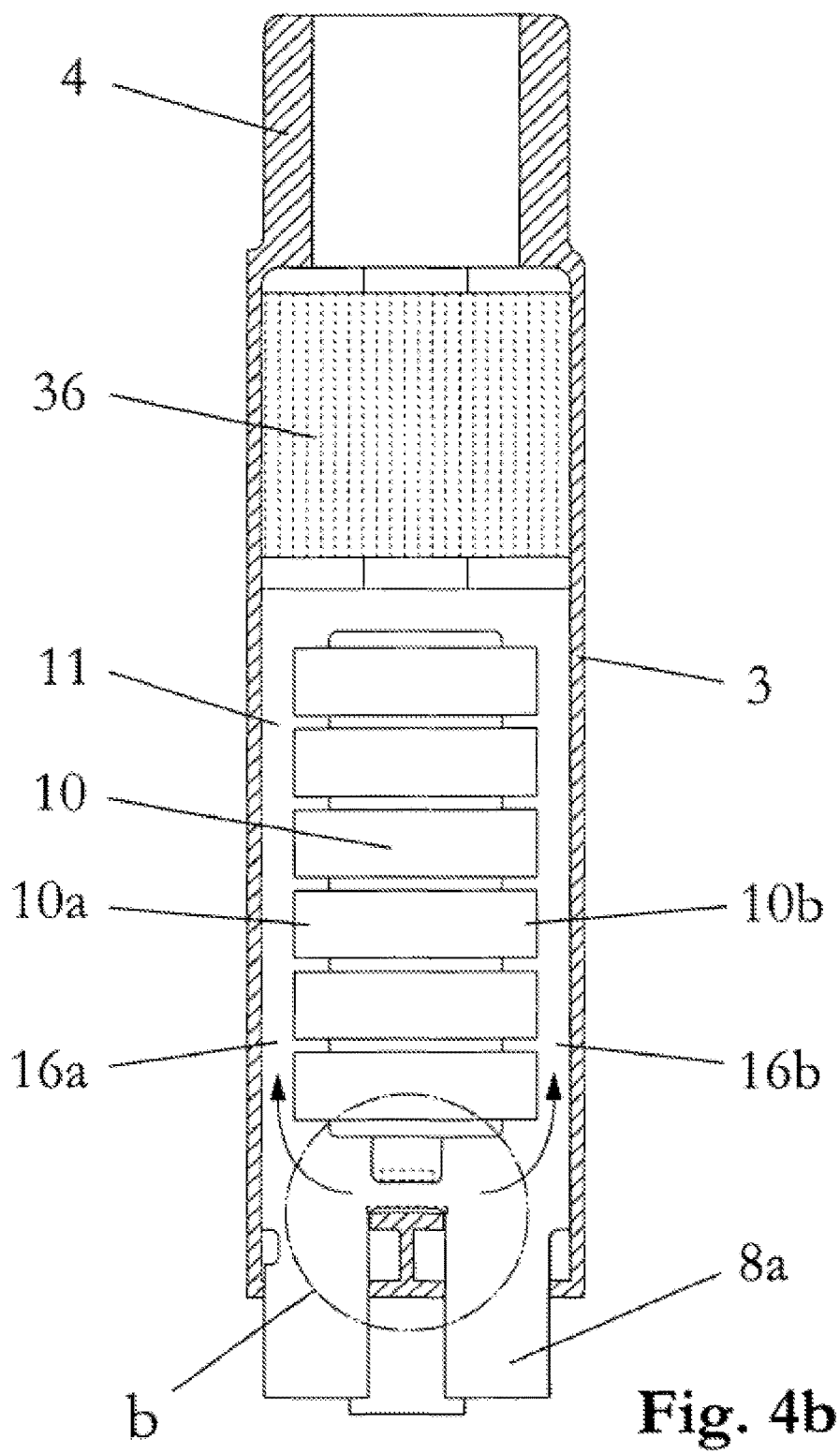
Figure 4C:
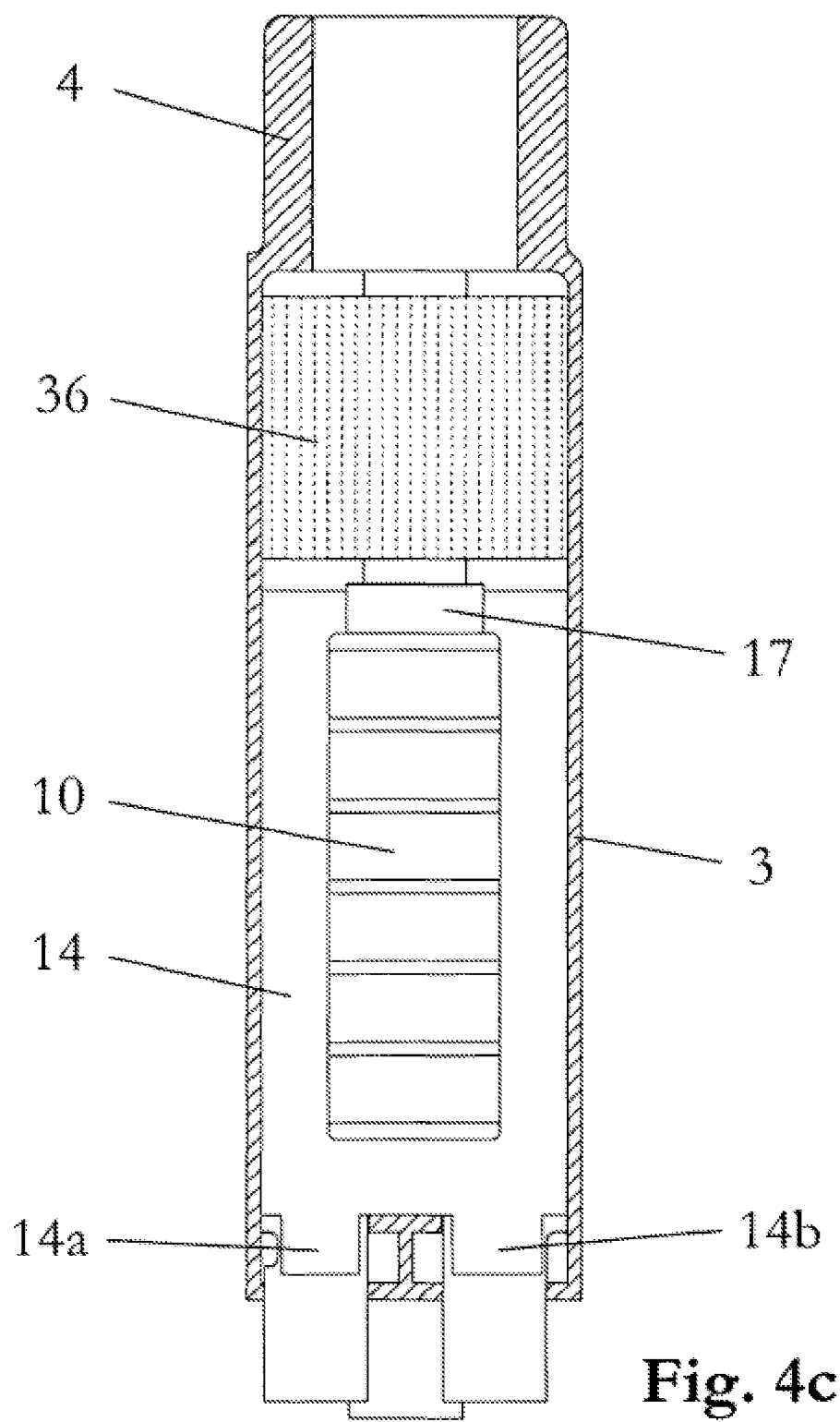
Figure 7:
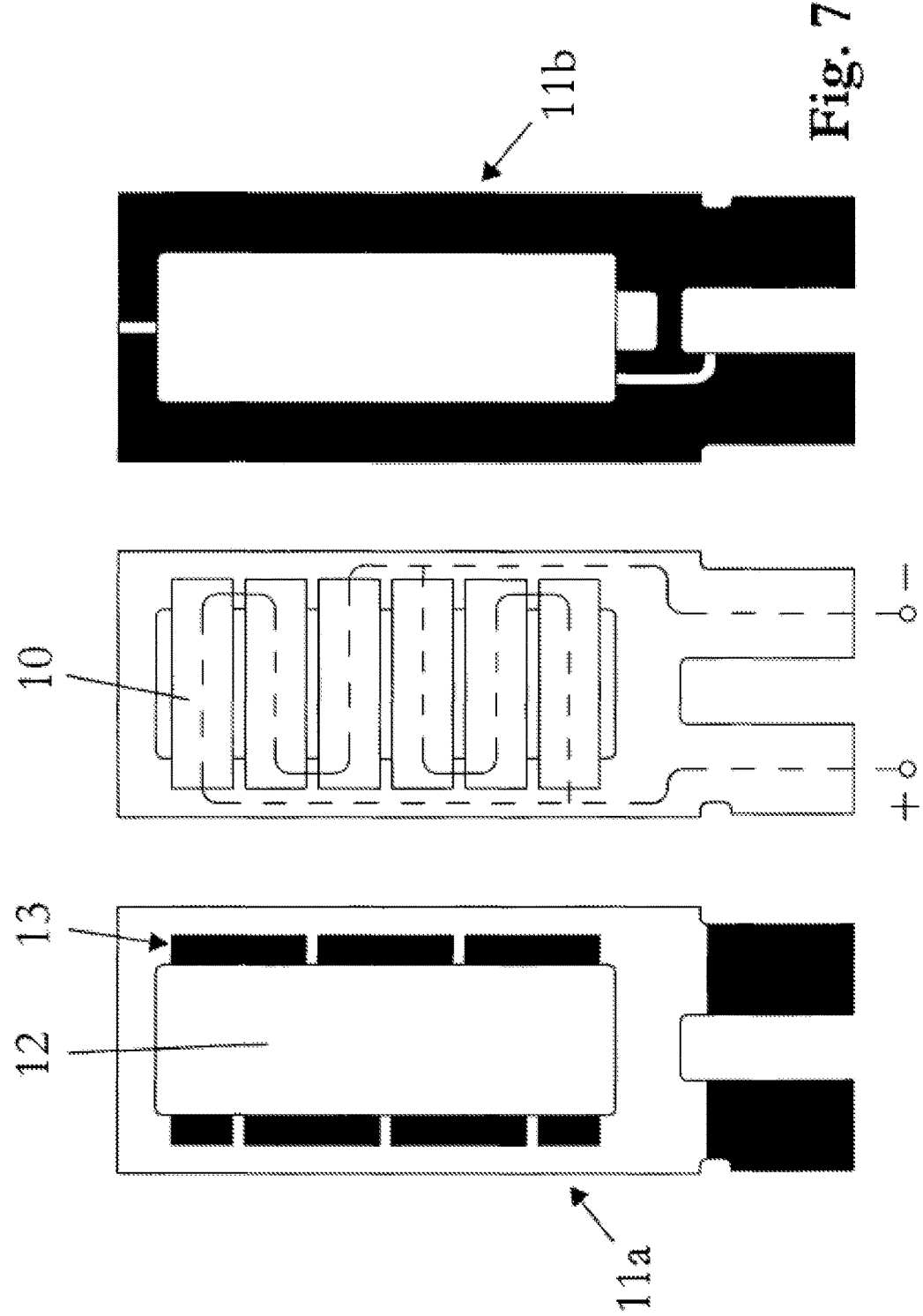
FIG. 7, a carrier plate configured as a multilayer printed circuit board.

As is best shown by FIG. 4b and FIG. 7, the sheetlike composites 10 are mounted by two end segments 10a, 10b on a carrier plate 11. The carrier plate 11 has a large recess 12, which the composites 10 span with no contact. In the specific sample embodiment, the carrier plate 11 is configured as a printed circuit board, especially a multilayer printed circuit board. Basically all known circuit board materials are suitable as the material for the circuit board 11, especially material types FR1 to FR5. The sheetlike composites 10 are electrically contacted in the region of the end segments 10a, 10b on printed conductor tracks 13 of the circuit board 11. In FIG. 7, the conductor tracks 13 are represented as dark areas. In the case of the above-mentioned metal foil composites, the electrical contacting occurs preferably by a soldering at the foil side, optionally after pretreatment with a suitable flux. Special steels of material grades AISI 304 and AISI 316 can be soldered with no problem using a solder concentrate with the brand name "50505-Nirosta" from Stannol GmbH, www.stannol.de, for example. Alternatively, the electrical contacting can consist of a glue connection by means of an electrically conducting adhesive, such as an epoxy-based glue containing silver. The placement of the sheetlike composites 10 on the printed circuit board 11 and their contacting are done fully automatic, in which methods of the printed circuit industry can be used, which methods are also suitable for a mass production.

The printed circuit board 11 protrudes from the housing 3 in the form of the already mentioned insertion tongues 8a. The two insertion tongues 8a serve to channel the electrical energy into the inhaler component 2. The electrical energy is supplied to the composites 10 via the conductor tracks 13. In FIG. 7, the conductor tracks 13 are arranged on both the front side 11a and the back side 11b of the circuit board 11, where the front side 11a is the mounting side, that is, the side on which the composites 10 are contacted. Additional conductor tracks can also be arranged optionally in intermediate layers. The individual conductor track layers are advisedly joined together by means of so-called through contact points of the prior art. Moreover, the current flow is represented in FIG. 7. Accordingly, in the specific example, each time three composites 10 are hooked up in series. In this way, one can influence the resulting heating resistance and thus the heating power and rate of evaporation within certain limits. It can also be provided that the individual electrical resistances of the six composites 10 are of different magnitude, for example, by varying the thickness of the metal foil. In this way, one can also make the evaporation process dependent on location, as in a cigarette.

Figure 4D:
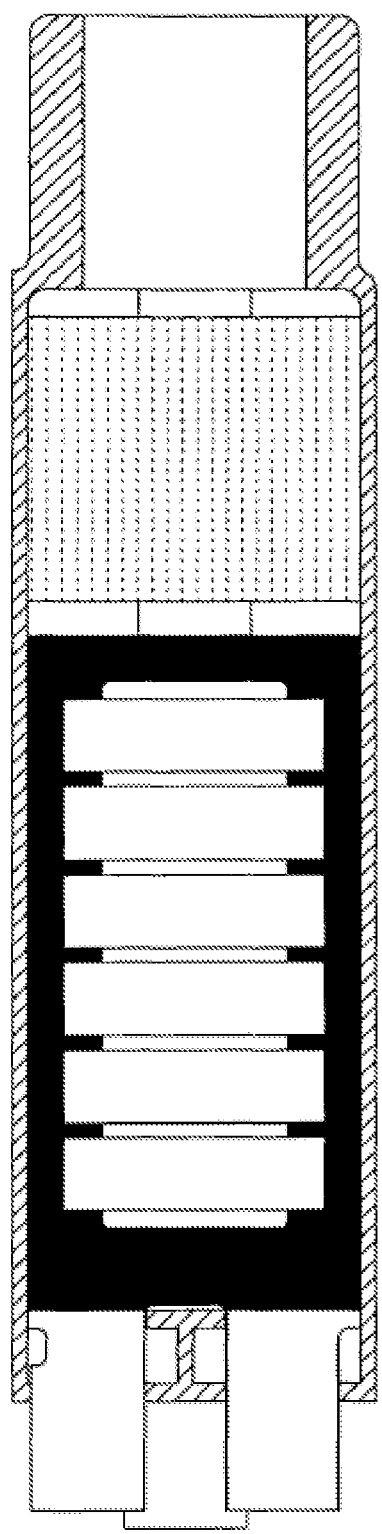

On the front side 11a of the printed circuit board 11 is placed an essentially platelike upper part 14, preferably consisting of plastic (see FIG. 4c and FIG. 8-10). The upper part 14 has a recess 15, which in terms of size and arrangement correlates with the recess 12 in the circuit board 11. In the simplest case, the upper part 14 rests directly on the end segments 10a, 10b of the sheetlike composites 10. In this way, the upper part 14 together with the circuit board 11 forms a capillary gap 16, whose clear width or gap width corresponds essentially to the thickness of the sheetlike composites 10 (see FIG. 9 and FIG. 10). Typically, the gap width is 0.2 mm. In FIG. 4d, the surface coverage of the capillary gap 16 is shown as a dark surface. The upper part 14 is fastened to the circuit board 11 by a glue connection, specifically, by two projections 14a, 14b and by a support bracket 17.

Figure 8:
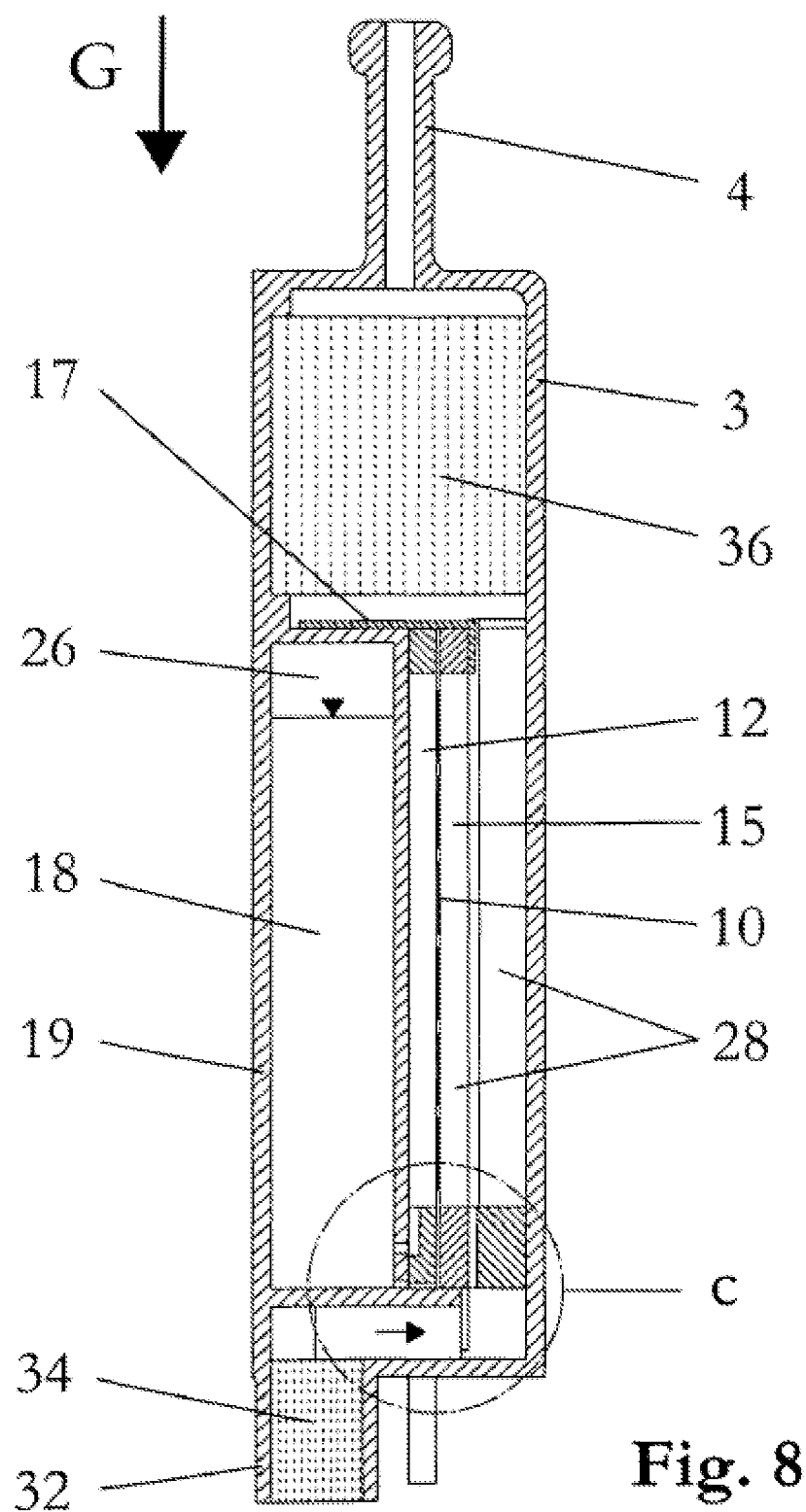
FIG. 8, a sectional view of the interchangeable inhaler component along line B-B in FIG. 3b.

The circuit board 11 rests by its back side 11b on a liquid container 19 containing the liquid material 18 (see FIG. 4a/4b, FIG. 8 and FIG. 10). The liquid container 19 or its wall is formed by the housing 3 and has a rectangular shape. The circuit board 11 is preferably fastened by means of a glue connection to the wall of the liquid container. The filling of the liquid container 19 with the liquid material 18 is done at the factory at the end of the manufacturing process, preferably through a small hole in the container wall (not shown) in a fully automatic process using a cannula and a dispensing unit. The hole is sealed after the filling, for example, it is melted shut, and the entire inhaler component 2 is packed air tight.

Figure 5:
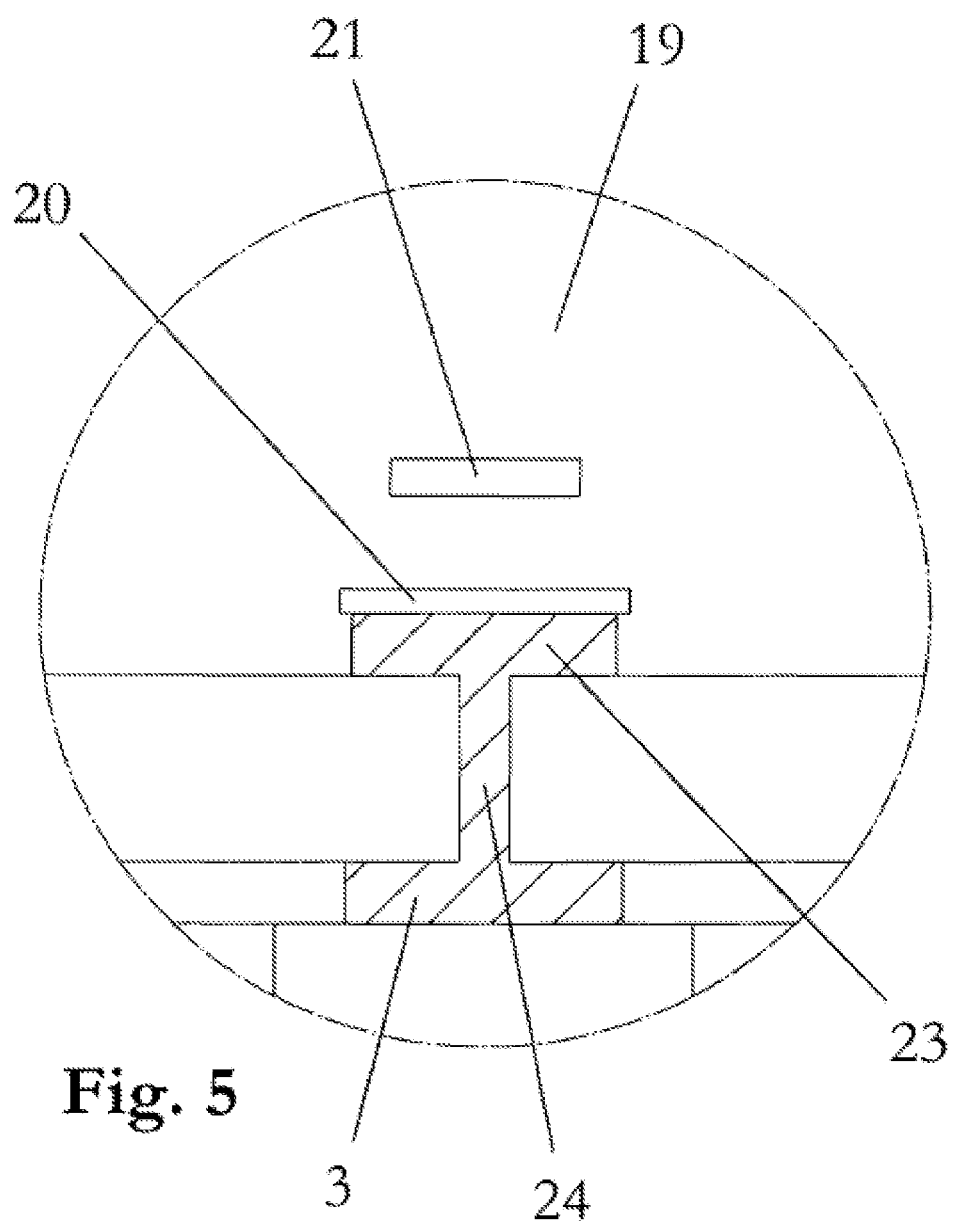
FIG. 5, feature a from FIG. 4a in a magnified representation.
Figure 6:
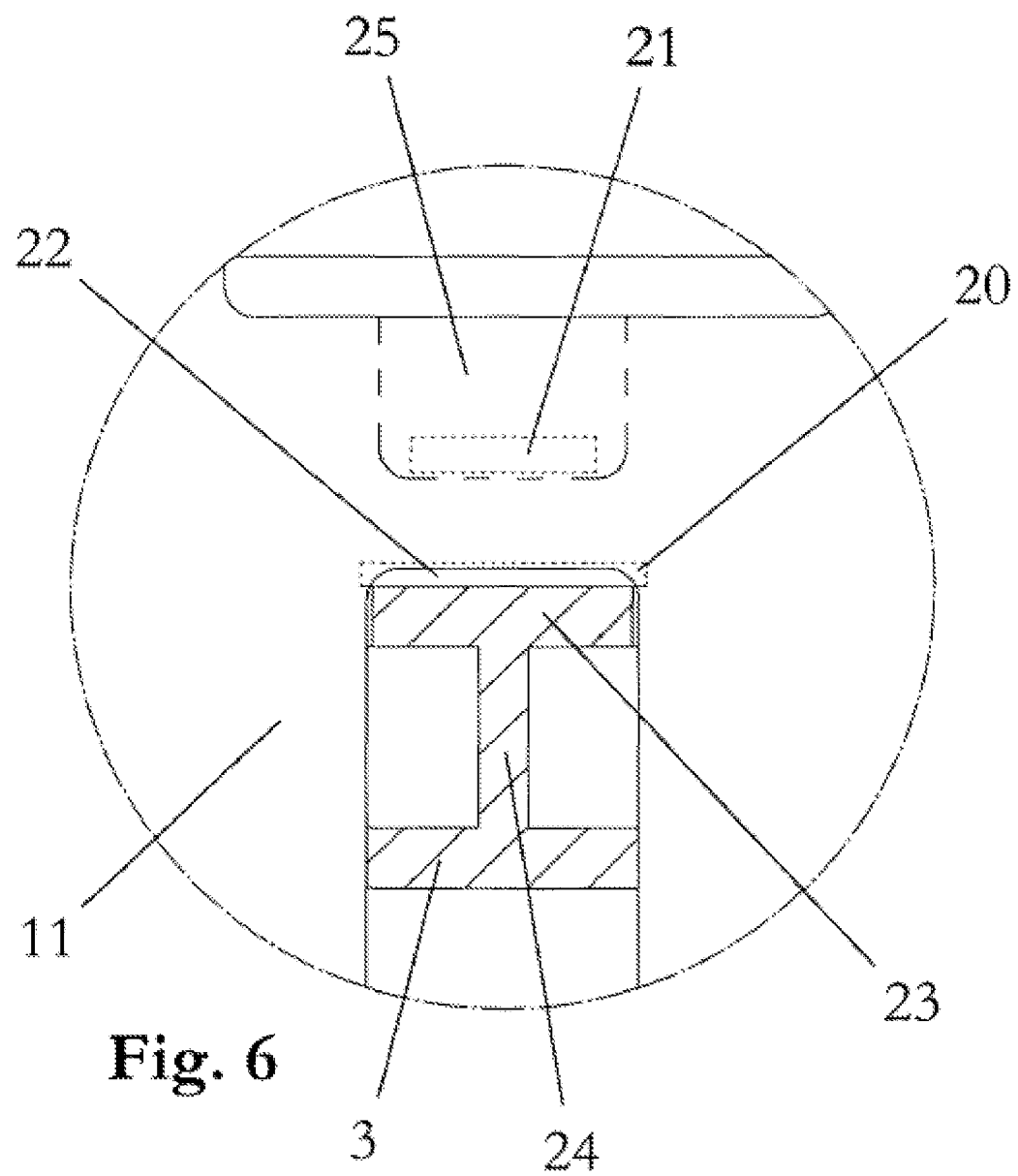
FIG. 6, feature b from FIG. 4b in a magnified representation.
Figure 9:
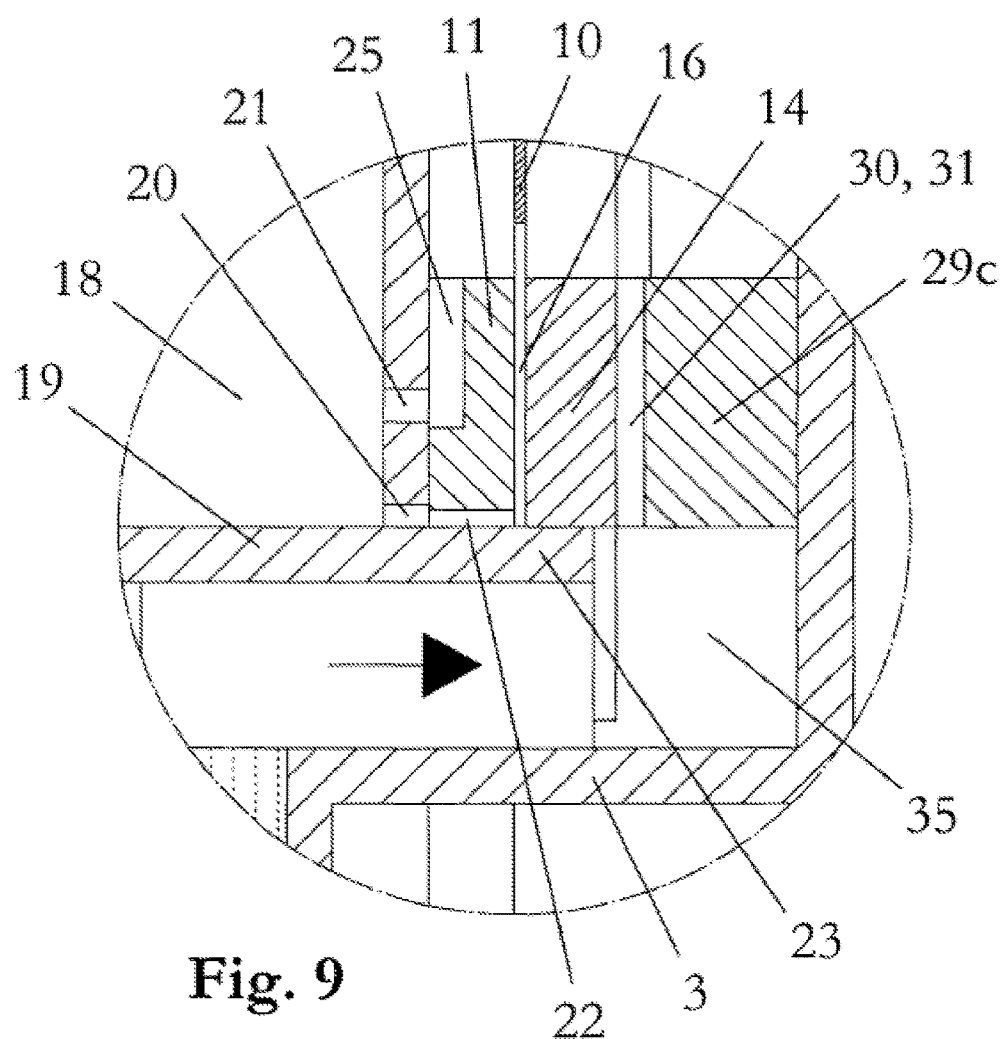
FIG. 9, feature c from FIG. 8 in a magnified representation.

The liquid container 19 has at its lower end two closely arranged openings—the supply opening 20 and the vent opening 21 (see FIG. 5, FIG. 6 and FIG. 9). The supply opening 20 corresponds with an admission opening 22 that is formed by the edge of the printed circuit board 11 and a shoulder 23 of the wall of the liquid container (see FIG. 6 and FIG. 9). The shoulder 23 at the same time forms an end stop for the upper part 14. For stiffness, the shoulder 23 is braced by a web 24 against the housing 3. The supplying of the capillary gap 16 with the liquid material 18 occurs via the supply opening 20 and the admission opening 22 and is driven by the capillary forces working in the capillary gap 16. In order for these capillary forces to work at all, it is necessary for the liquid material 18 to thoroughly wet all exposed surfaces. To ensure this, the affected parts—namely, the liquid container 19, the printed circuit board 11 and composites 10 and the upper part 14—must be made hydrophilic in a suitable process even before the assembly process. Suitable processes are hydrophilization in oxygen plasma and hydrophilization by means of plasma polymerization. Both processes are offered in the course of contract manufacture by the firm Diener electronic GmbH u. Co. KG, www.plasma.de, for example. The mentioned firm is furthermore also capable of planning and constructing suitable customer-specific plants for a mass production.

The vent opening 21 corresponds with a vent groove 25 worked into the printed circuit board 11, which communicates in turn via the recess 12 with an inner space standing at atmospheric pressure. The vent opening 21 and the vent groove 25 bring about a pressure equalization, so that each portion of liquid material 18 that arrives in the capillary gap 16 is immediately replaced by an equal-volume portion of air.

The overlapping arrangement of the printed circuit board 11 and the liquid container 19, as well as the above-described arrangement of the supply opening 20, the admission opening 22 and the vent opening 21, make it possible to assure a relatively large capillary gap surface, which is necessary when several composites 10 alongside each other need to be supplied with the liquid material 18. The danger of liquid material 18 escaping at any site due to the action of gravity can be largely prevented. In the vertical position of the inhaler component 2 shown in FIG. 8 (an arrow shows the direction of gravity), approximate atmospheric pressure prevails in the vent opening 21, since the capillary gap 16 does not expand further at the bottom in relation to the admission opening 22 (see FIG. 4d). When the inhaler component 2 is placed on its head (the mouthpiece 4 is pointing downward), the liquid column in the capillary gap 16 can induce a partial vacuum, but this cannot act backwards on the liquid material 18 in the liquid container 19, because an air cushion in the liquid container 19 interrupts the capillary coupling. When the liquid container 19 is being filled at the factory, it is only necessary to pay attention so that a small air volume 26 remains to form the air cushion in the container.

Before discussing in greater detail the mode of operation of the inhaler according to the invention, some further parts of the inhaler component 2 shall be described below. Even though these parts might not be immediately relevant to the invention, their description will help better understand the functioning of the invented inhaler component as a whole, and guarantee even more the implementability of the invention: between the upper part 14 and the housing 3 are arranged two open-pore absorbent sponges 27a, 27b (see FIG. 4e and FIG. 10). The space between the sponges together with the recess 15 forms a chamber 28 (also see FIG. 8), in which the actual formation of the vapor/air mixture and/or condensation aerosol takes place. The sponges 27a, 27b take up in their pores the condensate deposits formed from the vapor phase and prevent freely movable condensate build-up in the inhaler component 2, which might impair the function of the inhaler component. Such condensate build-up could also represent a problem from a hygiene standpoint, if it could get into the oral cavity of the user through the mouthpiece 4. The sponges 27a, 27b preferably consist of a fine-pore fiber composite. The firm Filtrona Fibertec GmbH, www.filtronafibertec.com, specializes in the production of such fiber composites, in which both cellulose acetate fibers bound by means of triacetin and thermally bound polyolefin and polyester fibers are processed.

Figure 4E:
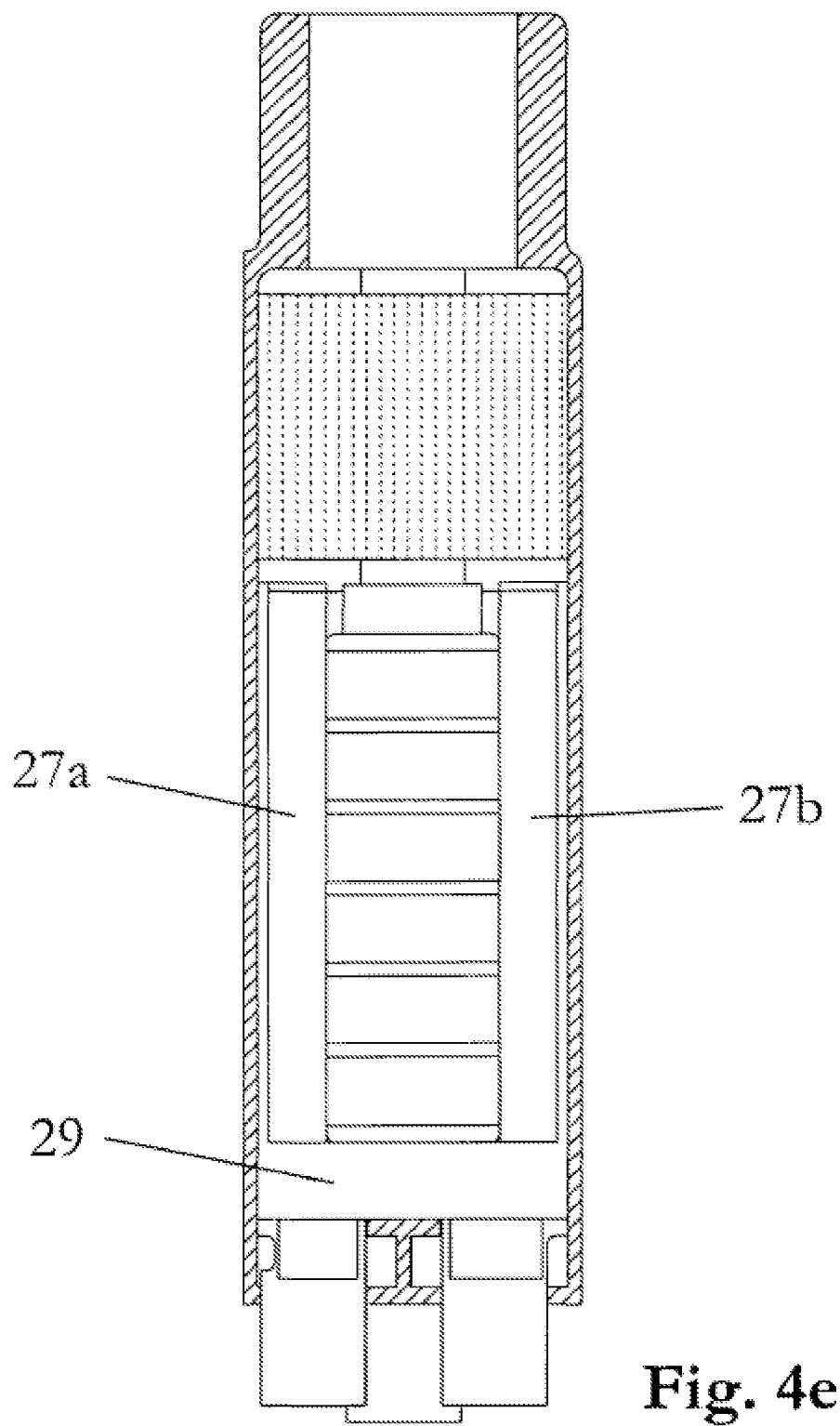

The sponges 27a, 27b rest on angle profiles 29a, 29b formed by a U-shaped carrier 29 (see FIG. 4e and FIG. 10). The carrier 29 is joined to the upper part 14 by a glue connection. The carrier 29 and the angle profiles 29a, 29b preferably consist of a hydrophobic plastic. The hydrophobic material acts like a liquid barrier and makes sure that no liquid material 18 can get to the sponges 27a, 27b by capillary effects. In the leg 29c which joins the angle profiles 29a, 29b, an indentation 30 is worked into the side facing the upper part 14, which together with the upper part 14 forms an air nozzle 31 (see FIG. 9 and FIG. 10). The air nozzle 31, as presented in greater detail below, serves to bring ambient air into the chamber 28. So that condensate build-up does not block the air nozzle 31, it is recommended to glue a thin hydrophobic adhesive tape (not shown) onto the upper part 14 in the area of the air nozzle 31.

The supply of ambient air to the inhaler component 2 to form the vapor/air mixture and/or condensation aerosol occurs through an intake snorkel 32 formed by the housing 3 (see FIG. 3a/3b and FIG. 8). The intake snorkel 32 is arranged on the side of the inhaler component 2 opposite the mouthpiece 4. This position best protects against entry of rain water. In the coupled state, the intake snorkel 32 of the inhaler component 2 protrudes through a hole 33 formed by the main housing 5 of the inhaler part 1 (see FIG. 2). A flow throttle 34 is located in the intake snorkel 32. The flow throttle 34 has the purpose of creating a flow resistance, which is similar to that of a cigarette, so that the user in drawing on it experiences a similar drawing resistance as when drawing on a cigarette. Specifically, the flow resistance for a flow rate of 1.05 L/min should lie in the range of 8 to 16 mbar and have the most linear possible characteristic. The flow throttle 34 is required when the formed vapor/air mixture and/or condensation aerosol is supposed to be furnished as in a cigarette, namely, by drawing it into the oral cavity (draught volume: around 20 to 80 mL), optionally followed by inhaling into the lungs. This mode of operation is primarily recommended when the liquid material 18 contains nicotine. However, the flow throttle 34 is eliminated when the inhaler is supposed to provide a direct lung inhalation in a single step, as is the case with most medical inhalers. The flow throttle 34 preferably consists of a fiber composite similar to a cigarette filter, the density of the material being attuned to the aforementioned flow characteristic. Once again, the material can be ordered from the firm Filtrona Fibertec GmbH, www.filtronafibertec.com.

In what follows, the functioning of the inhaler shall be described in detail: a user couples a new inhaler component 2 to the reusable inhaler part 1. The electrical circuit 7 registers the coupling and allows if appropriate the performance of certain preparatory operations, such as one or more evaporation cycles with the goal of supplying the composites 10 with fresh liquid material 18 and/or to produce steady-state conditions. As soon as these operations are completed, the electrical circuit 7 signals the readiness of the inhaler, for example, by a light-emitting diode. The user brings the mouthpiece 4 of the inhaler up to his mouth and activates the switch 7a. At the same time, he begins to draw on the mouthpiece 4. The partial vacuum created in this way has the effect that air flows from the surroundings into the intake snorkel 32. After the air has passed through the flow throttle 34, the flow diverges at a right angle (see arrow in FIG. 8 and FIG. 9) and issues into a plenum chamber 35, where the air collects and is then smoothly supplied to the slitlike air nozzle 31. The air flow is accelerated in the air nozzle 31 and enters the chamber 28 with a high exit velocity.

The activating of the switch 7a has the effect that the circuit 7 turns on the heating current. The heating current is preferably switched on by means of a power MOSFET, while the supplied power can be adapted to the particular requirements by a clock pulse (duty cycle). This adapting can also be done within certain limits by the user with an interface, which enables him to influence the quantity of aerosol or smoke produced. The heating current is turned on for a preset period of time ("heating period"), which is typically 1.0 to 1.8 seconds. The heating current is supplied to the composites 10 via the insert tongues 8a and the conductor tracks 13 of the circuit board 11 and brings about an instant heat-up of the composites 10 and the liquid material 18 stored in the wicks, whereupon the liquid material 18 evaporates. The vapor is emitted into the chamber 28, where it mixes with the air flowing in through the air nozzle 31. The arrangement and dimensioning of the air nozzle 31 brings about a smooth and quick flow across the composites 10. This ensures that the vapor given off by the composites 10 experiences approximately the same mixing conditions all around, and the mixture of vapor and air is intimate. The air produces a cooling of the vapor, so that a condensation aerosol can also be formed, insofar as the evaporated liquid material 18 contains substances with sufficiently low vapor pressure—so-called aerosol-forming substances. A typical example of such aerosol-forming substances is glycerol.

The vapor/air mixture and/or condensation aerosol formed in the chamber 28 finally flows, in the sample embodiment, through yet another cooler 36 before it is presented to the user for inhalation through the mouthpiece 4 (see FIG. 4e and FIG. 8). The cooler 36 can consist, for example, of a porous filler material, a fleecelike fiber material, or an open-cell foam material whose pores are permeated by the formed vapor/air mixture and/or condensation aerosol. The cooler 36 can also be multistage, wherein the individual cooler stages have different properties. If the material being evaporated contains nicotine, it can be advantageous to coat the cooler material of at least one cooler stage with a suitable absorbent, such as citric acid. The absorbent removes volatile nicotine fractions from the flowing condensation aerosol, such as would otherwise be deposited in the oral cavity and in the throat, which is neither pharmacokinetically nor organoleptically desirable. Moreover, fragrances such as menthol can be added to the cooler material.

Suitable fleecelike fiber materials can be ordered, for example, from the firm Freudenberg Vliesstoffe KG, www.freudenberg-filtercom. The material consisting of polyolefin fibers and marketed under the brand Viledon® filter mats is prepared by customer specification, and the material properties can be adjusted so that the end product is largely permeable to the fine particles of the condensation aerosol created. A suitable foam material can be ordered, for example, from the firm Dunlop Equipment, www.dunlop-equipment.com. This supplier offers Ni and NiCr foam under the brand name Retimet® (Grade 80) with a porosity of 90 to 95% and a pore diameter from around 300 µm in sheet form up to thicknesses of 15 mm. According to verbal communication of the company representative, even somewhat more fine-pored foams can be manufactured from a technology standpoint. The metal foams, furthermore, can be additionally compacted by rolling processes. The sheets can be further processed by laser cutting or wire erosion. Ni foam and especially NiCr foam are distinguished by high strength and resistance to high temperatures and oxidation. These properties make it advisable to recycle and reuse the relatively costly metal foams at the end of the life cycle of the inhaler component 2. If the liquid material 18 contains nicotine, the inhaler component 2 should only be sold to the consumer at a reasonable deposit. This ensures that the major portion of the cooler 36, sponges 27a, 27b and liquid container 19, contaminated with nicotine residue, is properly disposed of and optionally recycled.

At the end of the heating period, the circuit 7 deactivates the switch 7a for a couple of seconds. The deactivation is reported to the user, for example, by a light-emitting diode and is necessary so that the composites 10 can cool down, and the wicks can again take up the liquid material 18. The liquid transport is originally induced by the capillarity of the composites 10 or their wicks. The wicks imbibe the liquid material 18 through the composite end segments 10a, 10b from the capillary gap branches 16a, 16b (see FIG. 4b and FIG. 10). The wicks are thus infiltrated from two sides. The removal of liquid material 18 from the capillary gap branches 16a, 16b induces in the capillary gap 16a capillary pressure, which has retroactive effect as far back as the liquid container 19, so that liquid material 18 can flow out from the liquid container 19 into the capillary gap 16 through the supply opening 20 and the admission opening 22 (see arrows in FIG. 4b). The quantity of liquid material 18 removed from the liquid container 19 is replaced by an equivalent quantity of air in the course of a pressure equalization. The pressure equalization occurs via the vent groove 25 and the vent opening 21. As soon as the composites 10 and wicks are fully infiltrated with the liquid material 18, the inhaler is ready for a new evaporation cycle.

Finally, we shall disclose as an example a nicotine-containing preparation of the liquid material 18, which was evaporated in the prototypes (see table 1). The condensation aerosol formed and delivered in this case came very close to the smoking of a conventional cigarette in terms of the pharmacological, pharmacokinetic and organoleptic effects. All the ingredients listed are also found in cigarette smoke.

TABLE 1

| Substance | CAS number | wt. % |
| --- | --- | --- |
| water | 7732-18-5 | 52.92 |
| ethanol | 64-17-5 | 3.80 |
| glycerol (E422) | 56-81-5 | 40.10 |
| nicotine | 54-11-5 | 1.60 |
| lactic acid (E270) | 50-21-5 | 0.29 |
| succinic acid (E363) | 110-15-6 | 0.32 |
| benzoic acid (E210) | 65-85-0 | 0.26 |
| acetic acid (E260) | 64-19-7 | 0.71 |
| | Total: | 100.00 |

It should also be pointed out that the invention is of course not limited to one or more sheetlike composites 10 according to the sample embodiment just described. The composites 10 can likewise be liner or threadlike in form. Neither do the composites necessarily have to be straight or regular, but instead they can have any given shape. Moreover, the composites can be electrically hooked up to each other in any desired way. Finally, the invention also covers devices in which the liquid container 19 can be separated from the housing 3, so that the liquid container 19 can be replaced by a new liquid container as soon as it is empty.

LIST OF REFERENCE SYMBOLS 1 reusable inhaler part
2 interchangeable inhaler component
3 housing
4 mouthpiece
5 main housing
6 battery
7 electrical circuit
7a switch
8a insertion tongues
8b insert sockets
9a guide tabs
9b guide slots
10 sheetlike composite
10a, 10b composite end segments
11 carrier plate, circuit board, multilayer circuit board
11a carrier plate front side
11b carrier plate back side
12 recess
13 conductor tracks
14 upper part
14a, 14b projections
15 recess
16 capillary gap
16a, 16b capillary gap branch
17 support bracket
18 liquid material
19 liquid container
20 supply opening
21 vent opening
22 admission opening
23 shoulder
24 web
25 vent groove
26 air volume, air cushion
27a, 27b open-pore absorbent sponges
28 chamber
29 U-shaped carrier
29a, 29b angle profiles
29c leg
30 indentation
31 air nozzle
32 intake snorkel
33 hole
34 flow throttle
35 plenum chamber
36 cooler

The invention claimed is:

1. An inhaler component for forming a vapor/air mixture and/or condensation aerosol by evaporation of a liquid material to form the vapor of the vapor/air mixture and optionally condensation of the formed vapor, comprising:
an electric heating element for evaporating a portion of the liquid material;
a wick with a capillary structure, which wick forms a composite with the heating element and is configured to automatically supply the heating element with the liquid material;
a carrier plate which carries the composite;
a capillary gap formed at least partly by the carrier plate, for the automatic supplying of the heating element with the liquid material, where an end portion of the wick extends into the capillary gap;
a liquid container containing the liquid material, from which the capillary gap is configured to draw the liquid material, wherein the carrier plate is mounted for at least a section on the liquid container; and
an essentially plate-like upper part located on an opposite side of the composite from the carrier plate and having a recess, the recess correlating in size and arrangement with a recess of the carrier plate.

2. The inhaler component according to claim 1, wherein the capillary gap at least partially covers the liquid container on the outside thereof, in a view perpendicular to the carrier plate.

3. The inhaler component according to claim 1, wherein the composite at least partially covers the liquid container on the outside thereof, in a view perpendicular to the carrier plate.

4. The inhaler component according to claim 3, wherein the liquid container has essentially the shape of a cuboid, and the carrier plate is mounted for at least a section on one side surface of the cuboid.

5. The inhaler component according to claim 1, wherein the upper part rests directly on end portions of the composite.

6. An inhaler, comprising the inhaler component according to claim 1.

* * * * *